United States Patent [19]

Vecchietti et al.

[11] Patent Number: 4,954,509
[45] Date of Patent: Sep. 4, 1990

[54] ISOQUINOLINE DERIVATIVES AND THEIR USE AS ANALGESICS

[75] Inventors: Vittorio Vecchietti; Giuseppe Giardina, both of Baranzate, Italy

[73] Assignee: Dr. Lo. Zambeletti S.p.A., Italy

[21] Appl. No.: 312,648

[22] Filed: Feb. 17, 1989

[30] Foreign Application Priority Data

Feb. 19, 1988 [GB] United Kingdom ............... 8803919.1
Jun. 24, 1988 [GB] United Kingdom ................. 8815089

[51] Int. Cl.$^5$ ..................... A61K 31/47; C07D 401.06
[52] U.S. Cl. .................................. 514/307; 514/222.5; 514/226.8; 514/228.2; 514/235.2; 514/290; 514/298; 514/309; 544/2; 544/5; 544/8; 544/55; 544/62; 544/96; 544/128; 546/79; 546/93; 546/108; 546/111; 546/143; 546/144; 546/145; 546/146; 546/147
[58] Field of Search ............... 546/146, 147, 143, 144, 546/145, 93, 108, 111, 79; 544/128, 2, 5, 8, 55, 62, 96; 514/307, 309, 235.2, 290, 298, 222.5, 226.8, 228.2

[56] References Cited

U.S. PATENT DOCUMENTS

| | | | |
|---|---|---|---|
| 4,232,160 | 11/1980 | Schut et al. | 546/146 |
| 4,753,952 | 6/1988 | Vecchietti et al. | 546/146 |
| 4,806,547 | 2/1989 | Giardina et al. | 546/147 |

FOREIGN PATENT DOCUMENTS

| | | |
|---|---|---|
| 0104604 | 4/1984 | European Pat. Off. |
| 0228246 | 7/1987 | European Pat. Off. |
| 0232989 | 8/1987 | European Pat. Off. |
| 2361390 | 6/1975 | Fed. Rep. of Germany. |
| 1447611 | 8/1976 | United Kingdom. |

OTHER PUBLICATIONS

"Chemical Abstracts", vol. 98, 1983, col. 98:89195m.
Jin, et al., "Chemical Abstracts", vol. 106, 1987, col. 106:4976c.
Giarding, et al., "Chemical Abstracts", vol. 108, 1988, col. 108:37666w.

*Primary Examiner*—Glennon H. Hollrah
*Assistant Examiner*—James H. Turnipseed
*Attorney, Agent, or Firm*—Jacobs & Jacobs

[57] ABSTRACT

A compound, or a solvate or salt thereof, of formula (I):

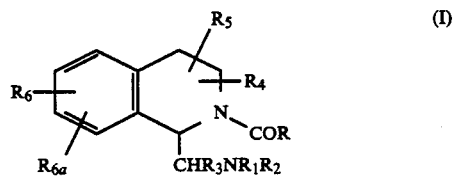

in which:

RCO is an acyl group in which the group R contains a substituted or unsubstituted carbocyclic aromatic or heterocyclic aromatic ring and $R_1$ $R_2$ are independently hydrogen, $C_{1-6}$ alkyl, $C_{2-6}$ alkenyl, $C_{3-6}$ cycloalkyl or $C_{4-12}$ cycloalkylalkyl groups or together form a $C_{2-8}$ branched or linear polymethylene or $C_{2-6}$ alkenylene group optionally substituted with a hetero-atom;

$R_3$ is hydrogen, $C_{1-6}$ alkyl, or phenyl, or $R_3$ together with $R_1$ forms a $-(CH_2)_3-$ or $-(CH_2)_4-$ group; $R_4$ and $R_5$, which may be the same or different and may be attached to the same or different carbon atoms of the isoquinoline nucleus, are each hydrogen, halogen, hydroxy, $C_{1-6}$ alkyl, aryl, or $R_4$ together with $R_5$ form a $-(CH_2)_p-$ group, where p is an integer of from 1 to 5 and one or more of the $-(CH_2)-$ moieties is optionally substituted by a $C_{1-6}$ alkyl group.

$R_6$ and $R_{6a}$, which may be the same or different, are each hydrogen, $C_{1-6}$ alkyl, $-CH_2OR_{6b}$, halogen, hydroxy, $C_{1-6}$ alkoxy, $C_{1-6}$ alkoxycarbonyl, thiol, $C_{1-6}$ alkylthio,

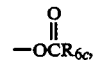

$-NHCOR_{6d}$, $-NHSO_2R_{6e}$, $-CH_2SO_2NR_6R_{6g}$, in which each of $R_{6b}$ to $R_{6g}$ is independently hydrogen, $C_{1-6}$ alkyl, aryl or aralkyl;

with the proviso that $R_4$, $R_5$, $R_6$ and $R_{6a}$ are not simultaneously hydrogen, is useful for the treatment of pain.

10 Claims, No Drawings

ISOQUINOLINE DERIVATIVES AND THEIR USE AS ANALGESICS

This invention is concerned with novel isoquinoline derivatives, processes for their preparation, and their use in medicine, particularly as analgesics.

Compounds which are Kappa-receptor agonists act as analgesics through interaction with Kappa opioid receptors. The advantage of Kappa-receptor agonists over the classical μ-receptor agonists, such as morphine, lies in their ability to cause analgesia while being devoid of morphine-like behavioural effects and addiction liability.

European Published Application No. 232989 discloses a group of isoquinoline derivatives which exhibit Kappa-receptor agonism without some of the behavioural effects of morphine and morphine analogues, and which are thus of potential therapeutic utility as analgesics.

A novel class of structurally related isoquinolines, in which the isoquinoline nucleus has at least one substituent, has now been discovered which also exhibit potent Kappa-receptor agonism without the aforementioned undesirable behavioural effects.

According to the present invention there is provided a compound, or a solvate or salt thereof, of formula (I):

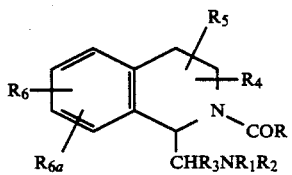

in which:
RCO is an acyl group in which the group R contains a substituted or unsubstituted carbocyclic aromatic or heterocyclic aromatic ring and $R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups or together form a $C_{2-8}$ branched or linear polymethylene or $C_{2-6}$ alkenylene group optionally substituted with a hetero-atom;

$R_3$ is hydrogen, $C_{1-6}$ alkyl, preferably methyl or ethyl, or phenyl, or $R_3$ together with $R_1$ forms a —(CH$_2$)$_3$— or —(CH$_2$)$_4$—, group;

$R_4$ and $R_5$, which may be the same or different and may be attached to the same or different carbon atoms of the isoquinoline nucleus, are each hydrogen, halogen, preferably fluorine, hydroxy, $C_{1-6}$ alkyl, preferably methyl or ethyl, aryl, preferably optionally substituted phenyl, or $R_4$ together with $R_5$ form a —(CH$_2$)$_p$— group, where p is an integer of from 1 to 5 and one or more of the —(CH$_2$)— moieties is optionally substituted by a $C_{1-6}$ alkyl group.

$R_6$ and $R_{6a}$, which may be the same or different, are each hydrogen, $C_{1-6}$ alkyl, —CH$_2$OR$_{6b}$, halogen, hydroxy, $C_{1-6}$ alkoxy, $C_{1-6}$ alkoxycarbonyl, thiol, $C_{1-6}$ alkylthio,

—NHCOR$_{6d}$, —NHSO$_2$R$_{6e}$, —CH$_2$SO$_2$NR$_{6f}$R$_{6g}$, in which each of R$_{6b}$ to R$_{6g}$ is independently hydrogen, $C_{1-6}$ alkyl, aryl or aralkyl;

with the proviso that $R_4$, $R_5$, $R_6$ and $R_{6a}$ are not simultaneously hydrogen.

In particular, $R_6$ and $R_{6a}$ may be hydroxy, methyl, methoxy, chloro, fluoro, methylthio or methoxy carbonyl.

Preferably one of $R_6$ and $R_{6a}$ is hydrogen, and the other substituent is suitably in the 5 or 8 position.

When used herein, the term 'carbocyclic aromatic group' includes single or fused rings, having 6 to 12 ring carbon atoms, and the term 'heterocyclic aromatic group' includes single or fused rings having 5 to 12 ring atoms, comprising up to four hetero-atoms in the or each ring, selected from oxygen, nitrogen and sulphur.

When the carbocyclic or heterocyclic group is a fused two ring system, one or both rings may be aromatic in character.

Suitably, one of the rings is aromatic and the other is non-aromatic.

The $C_{1-6}$ alkyl groups may be either straight or branched chain and examples are methyl, ethyl, propyl, n-butyl, n-pentyl or n-hexyl, preferably methyl.

Examples of $C_{2-6}$ alkenyl groups are 1- and 2- propenyl; an example of a $C_{3-6}$ cycloalkyl group is cyclopropyl, and an example of a $C_{4-12}$ cycloalkylalkyl group is cyclopropylmethyl.

When $R_1$ and $R_2$ together form a linear or branched polymethylene group, examples are propylene, butylene, pentylene or hexylene, preferably butylene or 1-methylbutylene. As an alkenylene group, $R_1$-$R_2$ may be so typically —CH$_2$—CH=CH—CH$_2$—. Examples of hetero-atoms are oxygen and sulphur, particularly oxygen, and a suitable hetero-atom substituted polymethylene group is —CH$_2$CH$_2$OCH$_2$CH$_2$—.

The group R preferably has the formula (II):

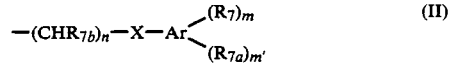

in which
n is 0, 1 or 2;
m is 0, 1 or 2;
m' is 0, 1 or 2, provided m+m'≦2
X is a direct bond, or O, S or NR$_8$ in which R$_8$ is hydrogen or $C_{1-6}$ alkyl;
Ar is a substituted or unsubstituted carbocyclic or heterocyclic aromatic group;
each of $R_7$ and $R_{7a}$ is $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, aryl, aralkyl, hydroxy, $C_{1-6}$ alkoxy, thiol, $C_{1-6}$ alkylthio, $C_{1-6}$ haloalkoxy, $C_{1-6}$ haloalkylthio, halogen, NO$_2$, CN, CF$_3$, —OCF$_3$, —OCHF$_2$, —OCF$_2$CF$_2$H, —OCCl$_2$CF$_3$, —COOR$_9$, —CONR$_{10}$R$_{11}$, —SO$_3$R$_{12}$, —SO$_2$NR$_{13}$R$_{14}$ and —COR$_{15}$ in which each of R$_9$ to R$_{15}$ is independently hydrogen, $C_{1-6}$ alkyl, aryl or aralkyl;

or, when m is 2 and m' is 0, two R$_7$'s form a $C_{2-6}$ polymethylene group;
and R$_{7b}$ is hydrogen or $C_{1-6}$ alkyl, such as methyl or ethyl.

Preferred halogens are F, Cl and Br.
When Ar is a carbocyclic aromatic group, it is preferably phenyl, and R$_7$ or R$_{7a}$ is preferably in the meta and/or para position.

Preferably $R_7$ or $R_{7a}$ is bromine, chlorine, $NO_2$ or $CF_3$, particularly in the meta- or para-position.

When Ar is a heterocyclic aromatic group, it is preferably thienyl.

X is typically oxygen or a direct bond, and n is typically 0 or 1.

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

The present invention also provides a process for the preparation of a compound of formula I which comprises reacting a compound of formula (III):

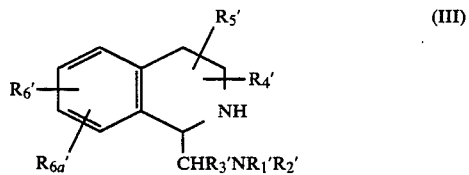

(III)

in which $R_1'$, $R_2'$, $R_3'$, $R_4'$, $R_5'$, $R_6'$ and $R_{6a}'$ are $R_1$, $R_2$, $R_3$, $R_4$, $R_5$, $R_6$ or $R_{6a}$ as defined for formula I, or each is a group or atom convertible to $R_1$, $R_2$, $R_3$, $R_4$, $R_5$, $R_6$ or $R_{6a}$, with a compound of formula R'CO.OH or an active derivative thereof, in which R' is as defined for formula (I), or a group convertible to R, to form a compound of formula (Ia)

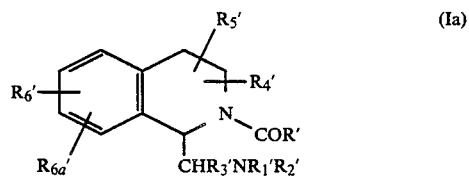

(Ia)

and then optionally performing one of the following steps:

(a) where R', $R_1'$, $R_2'$, $R_3'$, $R_4'$, $R_5'$, $R_6'$ and $R_{6a}'$ are other than R, $R_1$, $R_2$, $R_3$, $R_4$, $R_5$, $R_6$ or $R_{6a}$ converting R', $R_1'$, $R_2'$, $R_3'$, $R_4'$, $R_5'$, $R_6'$ and $R_{6a}'$ to R, $R_1$, $R_2$, $R_3$, $R_4$, $R_5$, $R_6$ or $R_{6a}$ to obtain a compound of formula (I), (b) where R', $R_1'$, $R_2'$, $R_3'$, $R_4'$, $R_5'$, $R_6'$ and $R_{6a}'$ are R, $R_1$, $R_2$, $R_3$, $R_4$, $R_5$, $R_6$ or $R_{6a}$ converting one R, $R_1$, $R_2$, $R_3$, $R_4$, $R_5$, $R_6$ or $R_{6a}$ to another R, $R_1$, $R_2$, $R_3$, $R_4$, $R_5$, $R_6$ or $R_{6a}$ to obtain a compound of formula (I), (c) forming a salt and/or solvate of the obtained compound of formula (I).

Suitable active derivatives of R'CO.OH are acid chlorides or acid anhydrides. Another suitable derivative is a mixed anhydride formed between the acid and an alkyl chloroformate.

For example, in standard methods well known to those skilled in the art, the compound of formula III may be coupled:

(a) with an acid chloride in the presence of an inorganic or organic base, (b) with the acid in the presence of dicyclohexyl carbodiimide, N-dimethylaminopropyl-N'-ethyl carbodiimide or carbonyl diimidazole, (c) with a mixed anhydride generated in situ from the acid and an alkyl (for example ethyl) chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

$R_1'$ and $R_2'$ may be alkyl groups and converted to $R_1$ or $R_2$ hydrogen atoms by conventional amine dealkylation. When $R_1'$ or $R_2'$ is benzyl or substituted benzyl it may be converted to an $R_1$ or $R_2$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The above described process can provide a diastereoisomeric mixture which can be subsequently separated into isomers by column chromatography.

The compound R'CO.OH is typically of the formula (IIa):

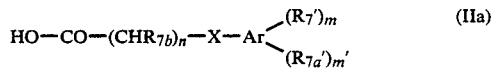

(IIa)

in which $R_7'$ and $R_{7a}'$ are $R_7$ and $R_{7a}$ as defined for formula (II), or a group or atom convertible to $R_7$ or $R_{7a}$, the other variables being as defined for formula (II).

Conversions of substituents $R_7'$ or $R_{7a}'$ on the aromatic group Ar to obtain $R_7$ or $R_{7a}$ are generally known in the art of aromatic chemistry. $R_7'$ is preferably $R_7$ and $R_{7a}'$ is preferably $R_{7a}$.

A preferred reagent is the equivalent acid halide of formula (IIb):

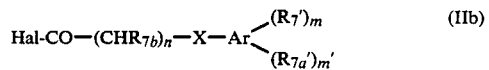

(IIb)

in which Hal is a halogen, typically chlorine or bromine.

The compounds of formula (I) may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

The compounds of formula I and their intermediates exist in more than one stereoisomeric form and the processes of the invention produces mixtures thereof.

The individual isomers may be separated one from another by resolution using an optically active acid such as tartaric acid. Alternatively, an asymmetric synthesis would offer a route to the individual form.

The compound of formula (III) may be obtained from a 3,4-dihydroisoquinoline compound of formula (IV) in which $R_3'$, $R_4'$, $R_5'$, $R_6'$ and $R_{6a}'$ have the meaning defined for formula (III), by treatment with an amine of formula $NHR'_1R'_2$ (where $R'_1$ and $R'_2$ are as defined above) followed by reaction of the formed compound of formula (V) with $NaBH_4$ or with hydrogen in the presence with the following reaction scheme:

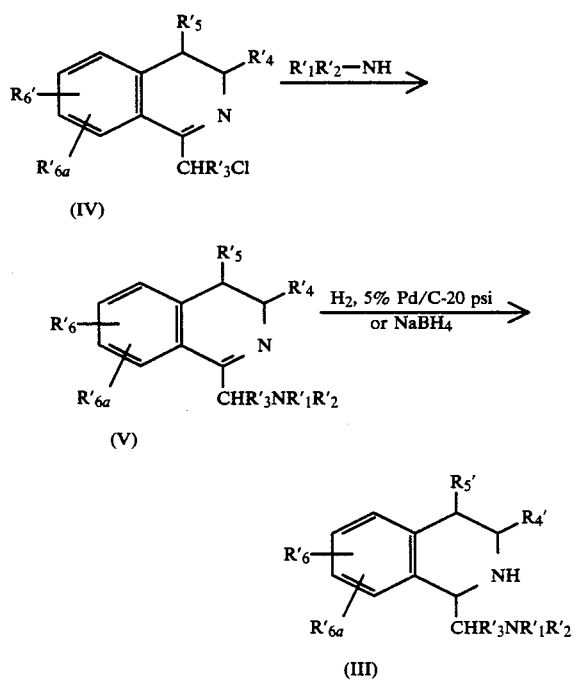

The compounds of formula (IV) are known compounds, or can be prepared from known compounds by known methods [J.O.C. 16, 1911, (1951)]. The compounds of formula (III) can be separated into their pure enantiomers by first protecting the NH group with an alkyl or benzyl chloroformate, resolving the compound thus formed using an active acid, such as O,O'-di-p-toluoyl tartaric acid, and subsequently deprotecting the optically active alkyl or benzyl carbamates in accordance with standard methods.

The intermediate compounds of formula (III) above are novel compounds and, as such, they form a further aspect of this invention.

The activity of the compounds of formula (I) in standard analgesic tests indicates that they are of therapeutic utility in the treatment of pain.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method of treating pain in mammals, particularly in humans, which comprises administering an effective amount of a compound of formula (I) or a pharmaceutically acceptable salt or solvate thereof, to a sufferer.

Compounds of this invention and their preparation are illustrated in the following Examples, while the Descriptions illustrate the preparation of intermediates.

DESCRIPTION 1

1-(pyrrolidin-1-yl)methyl-3-methyl-1,2,3,4-tetrahydroisoquinoline.

(Mixture of diastereoisomeric diamines)

3.9 g (16.96 mmoles) of 1-chloromethyl-3-methyl-3,4-dihydroisoquinoline hydrochloride [J. Org. Chem. 16, 1911–1920 (1951)] were added portionwise under nitrogen to a stirred solution of 6 g (85.00 mmoles) of pyrrolidine in 60 ml of methanol, cooled below $-5°$ C.

The stirring was continued 24 hours at room temperature and the nitrogen atmosphere maintained all the time.

The solution was then cooled to $0°$ C. and 1.0 g (125 mmoles) of sodium borohydride added.

After three hours 2 ml of conc. NaOH solution were added and the inorganic salts filtered off.

The filtrate was concentrated in vacuo to afford a residue which was treated with conc. NaOH solution and exhaustively extracted with diethyl ether.

The ethereal solution was filtered over celite, dried over $Na_2SO_4$ and the solvent evaporated in vacuo to dryness, to yield 3.8 g of the title compound, which was used without further purification for the following step.

Analogously, the following compounds were prepared:

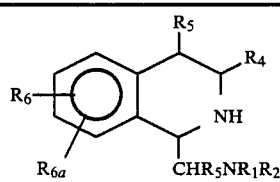

| R1 | R2 | R3 | R4 | R5 | R6 | R6a | MOLECULAR FORMULA | b.p. °C. / mmHg |
|---|---|---|---|---|---|---|---|---|
|  | | H | $CH_3$ | H | H | H | $C_{15}H_{22}N_2$ | * |
|  | | H | H | $CH_3$ | H | H | $C_{15}H_{22}N_2$ | * |

-continued

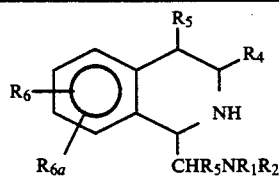

| R1 | R2 | R3 | R4 | R5 | R6 | R6a | MOLECULAR FORMULA | b.p. °C. / mmHg |
|---|---|---|---|---|---|---|---|---|
| ⌐⌐ | | H | H | H | 5-OCH$_3$ | H | C$_{15}$H$_{22}$N$_2$O | 143–147 / 0.3 |
| ⌐⌐ | | H | H | H | 5-Cl | H | C$_{14}$H$_{19}$ClN$_2$ | 140–143 / 0.2 |
| ⌐⌐ | | H | H | H | 5-F | H | C$_{14}$H$_{19}$FN$_2$ | 118–122 / 0.3 |
| ⌐⌐ | | H | H | H | 5-CH$_3$ | H | C$_{15}$H$_{22}$N$_2$ | 118–125 / 0.3 |
| CH$_3$ | CH$_3$ | H | H | H | 5-OCH$_3$ | H | C$_{13}$H$_{20}$N$_2$O | 113–118 / 0.3 |
| CH$_3$ | CH$_3$ | H | H | H | 5-Cl | H | C$_{12}$H$_{17}$ClN$_2$ | 110–114 / 0.2 |
| CH$_3$ | CH$_3$ | H | H | H | 6-OCH$_3$ | H | C$_{13}$H$_{20}$N$_2$O | 124–131 / 0.4 |
| CH$_3$ | CH$_3$ | H | H | H | 6-Cl | H | C$_{12}$H$_{17}$ClN$_2$ | 112–117 / 0.4 |
| ⌐⌐ | | H | H | H | 6-OCH$_3$ | H | C$_{15}$H$_{22}$N$_2$O | 152–156 / 0.3 |
| ⌐⌐ | | H | H | H | 6-Cl | H | C$_{14}$H$_{19}$ClN$_2$ | 143–147 / 0.4 |
| ⌐⌐ | | H | H | H | 7-OCH$_3$ | H | C$_{15}$H$_{22}$N$_2$O | 138–142 / 0.3 |
| ⌐⌐ | | H | H | H | 7-Cl | H | C$_{14}$H$_{19}$ClN$_2$ | * |
| CH$_3$ | CH$_3$ | H | H | H | 7-OCH$_3$ | H | C$_{13}$H$_{20}$N$_2$O | 109–113 / 0.3 |
| CH$_3$ | CH$_3$ | H | H | H | 7-Cl | H | C$_{12}$H$_{17}$ClN$_2$ | * |
| ⌐⌐ | | H | H | H | a | H | C$_{15}$H$_{22}$N$_2$O | 141–147 / 0.2 |
| ⌐⌐ | | H | H | H | b | H | C$_{14}$H$_{19}$ClN$_2$ | 142–162 / 0.4 |

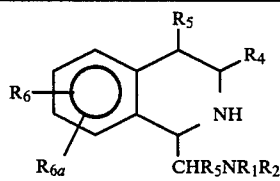

| R1 | R2 | R3 | R4 | R5 | R6 | R6a | MOLECULAR FORMULA | b.p. °C. / mmHg |
|---|---|---|---|---|---|---|---|---|
| —N(CH₂)₄— | | CH₃ | H | H | H | H | $C_{15}H_{22}N_2$ | 110–125 / 0.2 |
| CH₃ | CH₃ | CH₃ | H | H | H | H | $C_{13}H_{20}N_2$ | 93–103 / 0.4 |
| —N(CH₂)₄— | | H | H | H | 5-SCH₃ | H | $C_{15}H_{22}N_2S$ | * |
| —N(CH₂)₅— | | H | H | H | 5-OCH₃ | H | $C_{16}H_{24}N_2O$ | 150–155 / 0.3 |
| —N(CH₂)₄— | | H | H | H | 5-OCH₃ | 6-OCH₃ | $C_{16}H_{24}N_2O_2$ | 147–154 / 0.2 |
| —N(CH₂)₄— | | H | CH₃ ⸺TRANS⸺ CH₃ | | H | H | $C_{16}H_{24}N_2$ DIAST. A + DIAST. B | * |
| —N(CH₂)₅— | | H | CH₃ ⸺TRANS⸺ CH₃ | | H | H | $C_{17}H_{26}N_2$ DIAST. A + DIAST. B | * |
| —N(CH₂)₄— | | H | CH₃ ⸺CIS⸺ CH₃ | | H | H | $C_{16}H_{24}N_2$ DIAST. C | * |
| —N(CH₂)₄— | | H | H | C₆H₅ | H | H | $C_{20}H_{24}N_2$ | * |

* Used for the subsequent reaction without further purification
a Mixture of 6- and 8-OCH₃
b Mixture of 6- and 8-Cl

DESCRIPTION 2

1-dimethylaminomethyl-7-hydroxy-1,2,3,4-tetrahydroisoquinoline dihydrobromide.

1.0 g (4.55 mmoles) of 1-dimethylaminomethyl-7-methoxy-1,2,3,4-tetrahydroisoquinoline was heated two hours at 130° C. with 30 ml of 48% HBr.

The hydrobromic acid was then evaporated in vacuo and the residue was crystallized from 95% EtOH, to yield 1.00 g of the title compound.

$C_{12}H_{20}Br_2N_2O$
M.P. = >200
M.W. = 368.128

Elemental analysis: Calcd C,39.15; H,5.48; N,7.61; Br,43.22; Found C,38.88; H,5.62; N,7.54; Br,43.10.

Analogously, the following compounds were prepared:

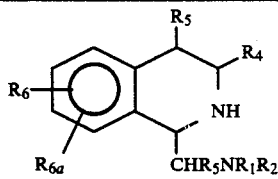

| R1 | R2 | R3 | R4 | R5 | R6 | R6a | MOLECULAR FORMULA (.2HBr) | MELTING POINT (°C., dec.) |
|---|---|---|---|---|---|---|---|---|
| pyrrolidinyl | | H | H | H | 5-OH | H | $C_{14}H_{20}N_2O$ | 280–281 |
| $CH_3$ | $CH_3$ | H | H | H | 5-OH | H | $C_{12}H_{18}N_2O$ | 253–254 |
| $CH_3$ | $CH_3$ | H | H | H | 6-OH | H | $C_{12}H_{18}N_2O$ | 224–226 |
| pyrrolidinyl | | H | H | H | 6-OH | H | $C_{14}H_{20}N_2O$ | 226–228 |
| pyrrolidinyl | | H | H | H | 7-OH | H | $C_{14}H_{20}N_2O$ | >200 |
| $CH_3$ | $CH_3$ | H | H | H | 7-OH | H | $C_{12}H_{18}N_2O$ | >200 |
| pyrrolidinyl | | H | H | H | c | H | $C_{14}H_{20}N_2O$ | — |
| piperidinyl | | H | H | H | 5-OH | H | $C_{15}H_{22}N_2O$ | 291–292 |
| pyrrolidinyl | | H | H | H | 5-OH | 6-OH | $C_{14}H_{20}N_2O_2$ | 251–252 | c Mixture of 6- and 8-OH

DESCRIPTION 3

1-(pyrrolidin-1-yl)methyl-2-benzyloxycarbonyl-5-methoxy-1,2,3,4-tetrahydroisoquinoline 2.6 g (10.57 mmoles) of 1-(pyrrolidin-1-yl)methyl-5-methoxy-1,2,3,4-tetrahydroisoquinoline were dissolved in 30 ml of acetone, containing 1.5 ml of water and 13 g (94.20 mmoles) of potassium carbonate.

2.5 ml (17.51 mmoles) of benzyl chloroformate were added dropwise at room temperature. After two hours the solvent was evaporated in vacuo to dryness; the residue was treated with 10% HCl and extracted with a mixture of 1:1 hexane/diethyl ether.

The acidic layer was treated with 40% NaOH and exhaustively extracted with diethyl ether. The organic solution was dried over $Na_2SO_4$ and the solvent evaporated in vacuo, to afford 3.8 g of the title compound, which was used in the subsequent step without further purification.
$C_{23}H_{28}N_2O_3$
M.W. = 380.470

DESCRIPTION 4

(−)-1-(pyrrolidin-1-yl)methyl-2-benzyloxycarbonyl-5-methoxy-1,2,3,4-tetrahydroisoquinoline 3.67 g (9.66 mmoles) of 1-(pyrrolidin-1-yl)methyl-5-methoxy-1,2,3,4-tetrahydroisoquinoline were dissolved in 80 ml of dry acetone. 4.10 g (10.12 mmoles) of (+)-O,O′-di-p-toluoyl-D-tartaric acid monohydrate, dissolved in 70 ml of acetone, were added to the hot solution of the racemic base. The diastereoisomeric salt crystallized on standing.
Yield = 1.73 g
M.P. = 156°–157° C.
$[\alpha]_D^{20} = +41.0$ (C=1, MeOH).
This salt was treated with $NH_4OH$ solution and extracted with ethyl acetate, to yield 0.773 g of the title compound as an oil.
$[\alpha]_D^{20} = -36.9$ (C=1, MeOH).

DESCRIPTION 5

(+)-1-(pyrrolidin-1-yl)methyl-2-benzyloxycarbonyl-5-methoxy-1,2,3,4-tetrahydroisoquinoline The mother liquors of the Description No. 4 were evaporated in vacuo to dryness; the residue was treated with 32% NH$_4$OH solution and exhaustively extracted with ethyl acetate, to afford 2.45 g (6.44 mmoles) of the enriched free base.

2.73 g (6.76 mmoles) of (−)-O,O'-di-p-toluoyl-L-tartaric acid monohydrate, dissolved in 100 ml of ethyl acetate, were added and the solution gently warmed for 15'.

The diastereoisomeric salt crystallized on standing and was recrystallized from abs. EtOH up to a constant rotatory power.

Yield=1.65 g
M.P.=156°–157° C.
$[\alpha]_D^{20} = -40.5$ (C=1, MeOH).

This salt was treated with NH$_4$OH solution and extracted with ethyl acetate, to yield 0.840 g of the title compound as an oil.

$[\alpha]_D^{20} = -38.2$ (C=1, MeOH).

DESCRIPTION 6

(+)-1-(pyrrolidin-1-yl)methyl-5-methoxy-1,2,3,4-tetrahydroisoquinoline acetate 0.840 g (2.21 mmoles) of (+)-1-(pyrrolidin-1-yl)methyl-2-benzyloxycarbonyl-5-methoxy-1,2,3,4-tetrahydroisoquinoline were hydrogenated in 90% CH$_3$COOH at 30 psi, 3 hours, at room temperature over 100 mg of 5% Palladium on activated charcoal.

The catalyst was filtered off and the filtrate evaporated in vacuo to yield 0.66 g of the title compound, which was used in the subsequent step without further purification.

DESCRIPTION 7

(−)-1-(pyrrolidin-1-yl)methyl-5-methoxy-1,2,3,4-tetrahydroisoquinoline acetate 0.773 g (2.03 mmoles) of (−)-1-(pyrrolidin-1-yl)methyl-2-benzyloxycarbonyl-5-methoxy-1,2,3,4-tetrahydroisoquinoline were hydrogenated in the same conditions of the Description No. 6, to yield 0.61 g of the title compound, which was used in the subsequent reaction without further purification.

DESCRIPTION 8

(+)-1-(pyrrolidin-1-yl)methyl-5-hydroxy-1,2,3,4-tetrahydroisoquinoline dihydrobromide 0.66 g (2.15 mmoles) of (+)-1-(pyrrolidin-1-yl)methyl-5-methoxy-1,2,3,4-tetrahydroisoquinoline acetate were heated two hours at 130° C. with 7 ml of 47% HBr solution.

The hydrobromic acid was evaporated in vacuo to yield 0.85 g of the title compound, which was used without further purification in the subsequent reaction.

DESCRIPTION 9

(−)-1-(pyrrolidin-1-yl)methyl-5-hydroxy-1,2,3,4-tetrahydroisoquinoline dihydrobromide 0.61 g (1.99 mmoles) of (−)-1-(pyrrolidin-1-yl)methyl-5-methoxy-1,2,3,4-tetrahydroiscquinoline acetate were treated with 47% HBr solution in the same conditions of the Description No. 8, to yield 0.75 g of the title compound, which was used without further purification in the subsequent reaction.

EXAMPLE 1

1-(pyrrolidin-1-yl)methyl-2-(3,4-dichlorophenyl)acetyl-3-methyl-1,2,3,4-tetrahydroisoquinoline hydrochloride ⅓ hydrate. Diastereoisomer CIS 3.8 g (16.52 mmoles) of 1-(1-pyrrolidinylmethyl)-3-methyl-1,2,3,4-tetrahydroisoquinoline—mixture of diastereoisomeric diamines—and 4.2 g (20.48 mmoles) of 3,4-dichlorophenylacetic acid were dissolved in 90 ml of dry chloroform.

8.5 g (41.26 mmoles) of dicyclohexylcarbodiimide, dissolved in 25 ml of chloroform, were added dropwise to this solution, at −5° C. The reaction mixture was allowed to reach room temperature, stirred 6 hours and left overnight.

The precipitated dicyclohexylurea was filtered off and the solution was evaporated in vacuo to dryness.

The residual oil was chromatographed on silica gel, eluting with CH$_2$Cl$_2$ containing increasing amounts of MeOH (0.2–0.6%), to afford 3.0 g of the least polar product which was dissolved in 70 ml of ethyl acetate and the solution brought to acidic pH with HCl/diethyl ether.

The precipitate was filtered, washed and dried, to yield 2.6 g of the title compound.
C$_{23}$H$_{26}$Cl$_2$N$_2$O.HCl.⅓H$_2$O
M.P.=185°–187° C.
M.W.=459.838
Elemental analysis: Calcd. C, 60.07; H, 6.06; N, 6.09; Cl, 23.13; Found C, 60.09; H, 5.99; N, 6.04; Cl, 23.17.
I.R. (KBr): 1650 cm$^{-1}$ (s); 1400 cm$^{-1}$ (s)
N.M.R. (CDCl$_3$) 300 Mhz: δ 11.59 (s) 1 H; 7.1–7.5 (m) 7 H; 6.15 (dd) 1 H; 1 4.63 (t) 1 H; 4.42 (m) 1 H; 4.10 (m) 1 H; 4.08 AB system, J =15.8 Hz 2 H; 3.71 (m) 1 H; 3.17 (m) 1 H; 3.11 (m) 1 H; 2.89 (m) 1 H; 2.76 (m) 1 H; 2.66 (m) 1 H; 2.31 (m) 2 H; 2.06 (m) 2 H; 1.65 (d) 3 H; 1.61 (s) H$_2$O.

The relative configuration of the compound was determined by NOE experiments.

EXAMPLE 2

1-(pyrrolidin-1-yl)methyl-2-(3,4-dichlorophenyl)acetyl-3-methyl-1,2,3,4-tetrahydroisoquinoline hydrochloride hemihydrate acetone. Diastereoisomer TRANS Continuing the elution of the chromatographic column described in the Example 1 with an increased amount of MeOH (0.6–2 %), 1 g of a second product was obtained.

This was dissolved in 30 ml of acetone and the solution brought to acidic pH with HCl/diethyl ether.

The precipitate was filtered, washed and dried, to yield 800 mg of the title compound.
C$_{23}$H$_{26}$Cl$_2$N$_2$O.HCl.½H$_2$O.CH$_3$COCH$_3$
M.P.=115°–118° C.
M.W.=520.919
Elemental analysis: Calcd. C, 59.94; H, 6.58; N, 5.37; Found C, 59.96; H, 6.21; N, 5.62.
I.R. (KBr): 1710 cm$^{-1}$ (m); 1640 cm$^{-1}$ (s).
N.M.R. (CDCl$_3$) 300 Mhz: δ 11.16 (s) 1 H; 7.10–7.50 (m) 7 H; 5.59 (t) 1 H; 4.75 (t) 1 H; 4.09 AB system 2H, J =16.3 Hz; 4.08 (m) 1 H; 3.80 (m) 1 H; 3.61 (m) 1 H; 3.31 (m) 1 H; 3.27 (m) 1 H; 2.85 (m) 1 H; 2.73 (dd) 1 H; 2.52 (m) 1 H; 2.16 (s) acetone; 2.13 (m) 2 H; 1.95 (m) 2 H; 1.76 (s) H$_2$O; 1.01 (d) 3 H.

The relative configuration of the compound was determined by NOE experiments.

EXAMPLE 3

1-(pyrrolidin-1-yl)methyl-2-(3,4-dichlorophenyl)acetyl-4-methyl-1,2,3,4-tetrahydroisoquinoline hydrochloride. Diastereoisomer TRANS 5.1 g (22.17 mmoles) of 1-(1-pyrrolidinylmethyl)-4-methyl-1,2,3,4—tetrahydroisoquinoline—mixture of diastereoisomeric diamines—and 5.1 g (24.88 mmoles) of 3,4-dichlorophenylacetic acid were dissolved in 100 ml of dry chloroform.

10 g (48.55 mmoles) of dicyclohexylcarbodiimide dissolved in 25 ml of chloroform were added dropwise to this solution at −5° C. The reaction mixture was allowed to reach room temperature, stirred 6 hours and left overnight.

The precipitated dicyclohexylurea was filtered off and the solution was evaporated in vacuo to dryness.

The residual oil was chromatographed on silica gel, eluting with $CH_2Cl_2$ containing increasing amounts of MeOH (0.2–0.6%), to afford 2.0 g of the least polar product which was dissolved in 50 ml of ethyl acetate and the solution brought to acidic pH with HCl/diethyl ether.

The precipitate was filtered, washed and dried, to yield 1.7 g of the title compound.
$C_{23}H_{26}Cl_2N_2O \cdot HCl$

M.P.=214°–217° C.
M.W.=453.833

Elemental analysis: Calcd. C, 60.87; H, 6.00; N, 6.17; Found C, 60.67; H, 6.09; N, 6.08;

I.R. (KBr): 1635 $cm^{-1}$ (s)

N.M.R. ($CDCl_3$) 300 Mhz: δ 11.4 (s) 1 H; 7.03–7.43 (m) 7 H; 6.09 (dd) 1 H; 4.25 (m) 1 H; 4.10 AB system 2 H, J=16.4 Hz; 4.00 (m) 1 H; 3.92 (m) 2 H; 3.65 (m) 1 H; 3.05 (m) 2 H; 2.89 (m) 1 H; 2.71 (m) 1 H; 2.25 (m) 2 H; 2.04 (m) 2 H; 1.31 (m) 3 H.

No NOE experiment was performed and the relative configuration has been deduced by comparison with the compound described in the next example.

EXAMPLE 4

1-(pyrrolidin-1-yl)methyl-2-(3,4-dichlorophenyl)acetyl-4-methyl-1,2,3,4-tetrahydroisoquinoline hydrochloride. Diastereoisomer CIS Continuing the elution of the chromatographic column described in the Example 3 with an increased amount of MeOH (0.6–2%), 5.5 g of a second product were obtained.

This was dissolved in 100 ml of ethyl acetate and the solution brought to acidic pH with HCl/diethyl ether.

The precipitate was filtered, washed and dried, to yield 4.8 g of the title compound.
$C_{23}H_{26}Cl_2N_2O \cdot HCl$

M.P.=220–222° C.
M.W.=453.833

Elemental analysis: Calcd. C, 60.87; H, 6.00; N, 6.17; Found C, 60.47; H, 6.10; N, 5.97

I.R. (KBr): 1645 $cm^{-1}$ (s)

N.M.R. ($CDCl_3$) 300 Mhz: δ 11.3 (s) 1 H; 7.05–7.50 (m) 7 H; 6.07 (dd) 1 H; 4.24 (m) 1 H; 4.12 (m) 1 H; 4.08 AB system 2 H, J=16 Hz; 4.00 (m) 1 H; 3.73 (m) 1 H; 3.32 (m) 1 H; 3.04 (m) 1 H; 2.96 (m) 1 H; 2.76 (m) 2 H; 2.28 (m) 2 H; 2.06 (m) 2 H; 1.30 (d) 3 H.

The relative configuration of the compound was determined by NOE experiments.

EXAMPLE 5

1-(pyrrolidin-1-yl)methyl-2-(3,4-dichlorophenyl)acetyl-5-hydroxy-1,2,3,4-tetrahydroisoquinoline 5.0 g (12.70 mmoles) of 1-(1-pyrrolidinylmethyl)-5-hydroxy-1,2,3,4-tetrahydroisoquinoline dihydrobromide, 3.4 g (16.58 mmoles) of 3,4- dichlorophenylacetic acid and 4.5 ml (32.02 mmoles) of $Et_3N$ were dissolved in 90 ml of dry chloroform.

5.3 g (25.73 mmoles) of cyclohexylcarbodiimide, dissolved in 25 ml of chloroform were added dropwise to the solution at −5° C. The reaction mixture was allowed to reach room temperature and heated at 60° C. 6 hours.

600 mg of 3,4-dichlorophenylacetic acid were added and the refluxing continued 6 hours. After cooling, the precipitated dicyclohexylurea and triethylamine hydrobromide were filtered off and the solution was evaporated in vacuo to dryness.

The residue was treated with 70 ml of 8% HCl and 30 ml of ethanol at 90° C. for two hours.

The precipitate was filtered off and the solution evaporated in vacuo to dryness. The residual oil was treated with (aq.), $NH_3$ extracted with ethyl acetate, dried, evaporated to dryness and chromatographed on silica gel, eluting with $CH_2Cl_2$ containing increasing amounts of MeOH (1–2.5%). 1.9 g of the product were obtained and crystallized from ethyl acetate as free base, to yield 1.6 g of the title compound.
$C_{22}H_{24}Cl_2N_2O_2$

M.P.=165°–167° C.
M.W.=419.342

Elemental analysis : Calcd. C, 63.00; H, 5.77; N, 6.68; Cl, 16.91; Found C, 62.82; H, 5.82; N, 6.62; Cl, 16.95

I.R. (KBr): 3250 $cm^{-1}$; 1625 $cm^{-1}$ (s); 1585 $cm^{-1}$ (s).

EXAMPLE 6

1-(pyrrolidin-1-Yl)methyl-2-(3,4-dichlorophenyl)acetyl-5-methoxy-1,2,3,4-tetrahydroisoquinoline Prepared as Ex. No. 1, from 1.2 g (4.88 mmoles) of 1-(pyrrolidin-1-yl)methyl-5-methoxy-1,2,3,4-tetrahydroisoquinoline, 1.1 g (5.37 mmoles) of 3,4-dichlorophenylacetic acid and 2.2 g (10.68 mmoles) of dicyclohexylcarbodiimide in 50 ml of dry methylene chloride.

The silica gel chromatographic column was eluted with $CH_2Cl_2$ containing increasing amounts of MeOH (0.2–1%), to afford 1.8 g of the product which was crystallized from hexane as free base to yield 1.6 g of the title compound.
$C_{23}H_{26}Cl_2N_2O_2$

M.P.=127°–129° C.
M.W.=433.368

Elemental analysis: Calcd. C,63.74; H,6.05; N,6.46; Cl,16.36 Found C,63.01; H,6.11; N,6.33; Cl,16.94

I.R. (KBr): 1635 (s); 1475 (s); 1455 (s) $cm^{-1}$

N.M.R. ($CDCl_3$) 80 Mhz: δ6.6–7.5 (m,6H); 5.8 (m,1H); 4.8 (m,1H); 3.8 (s,3H); 2.0–4.4 (m,15H).

EXAMPLE 7

1-(pyrrolidin-1-yl)methyl-2-(3,4-dichlorophenyl)acetyl-5-chloro-1,2,3,4-tetrahydroisoquinoline hydrochloride Prepared as Ex. No. 1, from 1.4 g (5.60 mmoles) of 1-(pyrrolidin-1-yl)methyl-5-chloro-1,2,3,4-tetrahydroisoquinoline, 1.4 g (6.83 mmoles) of 3,4-dichlorophenylacetic acid and 3.0 g (14.56 mmoles) of dicyclohexylcarbodiimide in 50 ml of dry chloroform.

The silica gel chromatographic column was eluted with CH$_2$Cl$_2$ containing increasing amounts of MeOH (0.2–1%), to afford 1.6 g of the product which was dissolved in 40 ml of ethyl acetate and the solution brought to acidic pH with HCl/diethyl ether.

The precipitate was filtered, washed and dried, to yield 1.3 g of the title compound.
C$_{22}$H$_{23}$Cl$_3$N$_2$O.HCl
  M.P.=226°–228° C.
  M.W.=474.256
  I.R. (KBr): 1650 (s) cm$^{-1}$
  N.M.R. (CDCl$_3$)80 Mhz: δ11.8 (s, 1H); 6.8–7.5 (m, 6H); 6.1 (m, 1H); 2.0–4.5 (m, 16H).

EXAMPLE 8

1-(pyrrolidin-1-yl)methyl-2-(3,4-dichlorophenyl)acetyl-5-fluoro-1,2,3,4-tetrahydroisoquinoline hydrochloride.

Prepared as Ex. No. 1, from 1.7 g (7.26 mmoles) of 1-(pyrrolidin-1-yl)methyl-5-fluoro-1,2,3,4-tetrahydroisoquinoline, 1.6 g (7.80 mmoles) of 3,4-dichlorophenylacetic acid and 3.2 g (15.53 mmoles) of dicyclohexylcarbodiimide in 60 ml of chloroform.

After the column chromatography (likewise that described for the previous compound), 2.6 g of the product were obtained, dissolved in 40 ml of ethyl acetate and the solution brought to acidic pH with HCl/diethyl ether.

The precipitate was filtered, washed and dried, to yield 2.3 g of the title compound.
C$_{22}$H$_{23}$Cl$_2$FN$_2$O.HCl
  M.P.=235°–237° C.
  M.W.=457.799
  Elemental analysis: Calcd. C, 57.72; H, 5.28; N, 6.12; Found C, 57.89; H, 5.25; N, 6.11
  I.R. (KBr): 1635 (s); 1465 (s) cm$^{-1}$

EXAMPLE 9

1-(pyrrolidin-1-yl)methyl-2-(3,4-dichlorophenyl)acetyl-5-methyl-1,2,3,4-tetrahydroisoquinoline hydrochloride.

Prepared as Ex. No. 1, from 1.4 g (6.08 mmoles) of 1-(pyrrolidin-1-yl)methyl-5-methyl-1,2,3,4-tetrahydroisoquinoline, 1.4 g (6.83 mmoles) of 3,4-dichlorophenylacetic acid and 2.6 g (12.62 mmoles) of dicyclohexylcarbodiimide in 50 ml of dry chloroform.

After the column chromatography (likewise that described for the previous compound), 2.3 g of the product were obtained, dissolved in 40 ml of ethyl acetate and the solution brought to acidic pH with HCl/diethyl ether.

The precipitate was filtered, washed and dried, to yield 2.2 g of the title compound.
C$_{23}$H$_{26}$Cl$_2$N$_2$O.HCl
  M.P.=220°–222° C.
  M.W.=453.833
  Elemental analysis: Calcd. C, 60.87; H, 6.00; N, 6.17; Found C, 60.82; H, 6.05; N, 6.11.
  I.R. (KBr): 1635 (s) cm$^{-1}$

EXAMPLE 10

1-dimethylaminomethyl-2-(3,4-dichlorophenyl)acetyl-5-hydroxy-1,2,3,4-tetrahydroisoquinoline.

Prepared as Ex. No. 5, from 4.5 g (12.2 mmoles) of 1-dimethylaminomethyl-5-hydroxy-1,2,3,4-tetrahydroisoquinoline dihydrobromide, 3.3 g (16.10 mmoles) of 3,4-dichlorophenylacetic acid, 4.3 ml (30.60 mmoles) of triethylamine and 5.1 g (24.75 mmoles) of dicyclohexylcarbodiimide in 120 ml of dry chloroform.

The working up of the reaction mixture and the chromatographic column of the crude product were carried out in the same manner described in Ex. No. 5.

2.1 g of the produce were obtained and crystallized, as free base, from ethyl acetate, to yield 1.5 g of the title compound.
C$_{20}$H$_{22}$Cl$_2$N$_2$O$_2$
  M.P.=163°–164° C.
  M.W.=393.306
  Elemental analysis: Calcd. C,61.07; H,5.64; N,7.12; Cl,18.03 Found C,61.12; H,5.64; N,7.07; Cl,17.85
  I.R. (KBr): 3150 (broad); 1620 (s); 1580 (s); 1460 (s); 1280 (s) cm$^{-1}$

EXAMPLE 11

1-dimethylaminomethyl-2-(3,4-dichlorophenyl)acetyl-5-methoxy-1,2,3,4-tetrahydroisoquinoline.

Prepared as Ex. No. 1, from 1.2 g (5.45 mmoles) of 1-dimethylaminomethyl-5-methoxy-1,2,3,4-tetrahydroisoquinoline, 1.3 g (6.37 mmoles) of 3,4-dichlorophenylacetic acid and 2.4 g (11.70 mmoles) of dicyclohexylcarbodiimide in 50 ml of dry methylene chloride.

The silica gel chromatographic column was eluted with CH$_2$Cl$_2$ containing increasing amounts of MeOH (0.2–1%), to afford 1.8 g of the product which was crystallized from hexane as free base, to yield 1.5 g of the title compound.
C$_{21}$H$_{24}$Cl$_2$N$_2$O$_2$
  M.P.=109°–111° C.
  M.W.=407.332
  Elemental analysis: Calcd. C,61.92; H,5.94; N,6.88; Cl,17.41 Found C,61.91; H,5.98; N,6.84; Cl,17.36
  I.R. (KBr): 1635 (s); 1585 (m); 1475,1465,1455 (s) cm$^{-1}$

EXAMPLE 12

1-dimethylaminomethyl-2-(3,4-dichlorophenyl)acetyl-5-chloro-1,2,3,4-tetrahydroisoquinoline hydrochloride.

Prepared as Ex. No. 1 , from 1.4 g (6.23 mmoles) of 1-dimethylaminomethyl-5- chloro -1,2,3,4-tetrahydroisoquinoline, 1.6 g (7.84 mmoles) of 3,.4-dichlorophenylacetic acid and 2.8 g (13.65 mmoles) of dicyclohexylcarbodiimide in 50 ml of dry chloroform.

The silica gel chromatographic column was eluted with CH$_2$Cl$_2$, containing increasing amounts of MeOH (0.2–1.5%), to afford 2.6 g of the product which was dissolved in 50 ml of ethyl acetate and the solution brought to acidic pH with HCl/diethyl ether.

The precipitate was filtered, washed and dried, to yield 2.4 g of the title compound.
C$_{20}$H$_{21}$Cl$_3$N$_2$O.HCl
  M.P.=241°–244° C.
  M.W.=448.220
  Elemental analysis: Calcd. C, 53.59; H, 4.95; N, 6.25; Found C, 53.28; H, 4.96; N, 6.12.
  I.R. (KBr): 1630 (s) cm$^{-1}$

EXAMPLE 13

1-dimethylaminomethyl-2-(3,4-dichlorophenyl)acetyl-6-hydroxy-1,2,3,4-tetrahydroisoquinoline.

Prepared as Ex. No. 5, from 5 g (13.58 mmoles) of 1-dimethylaminomethyl-6-hydroxy-1,2,3,4-tetrahydroisoquinoline dihydrobromide, 3.7 g (18.13 mmoles) of 3,4-dichlorophenylacetic acid, 5 ml (35.57 mmoles)

of triethylamine and 5.6 g (27.32 mmoles) of dicyclohexylcarbodiimide in 125 ml of dry chloroform.

The working up of the reaction mixture and the chromatographic column of the crude product were carried out in the same manner described in Ex. No. 5.

2.2 g of the product were obtained and crystallized, as free base, from 95% EtOH, to yield 1.6 g of the title compound.

$C_{20}H_{22}Cl_2N_2O_2$

M.P.=199°-200° C.

M.W.=393.306

Elemental analysis: Calcd. C,61.07; H,5.64; N,7.12; Cl,18.03 Found C,60.97; H,5.68; N,7.08; Cl,17.98

I.R. (KBr): 3320 (broad); 1630, 1615 (s); 1600 (m) 1440 (s); 1230 (s) cm$^{-1}$

EXAMPLE 14

1-dimethylaminomethyl-2-(3,4-dichlorophenyl)acetyl-6-methoxy-1,2,3,4-tetrahydroisoquinoline hydrochloride.

Prepared as Ex. No. 1, from 1.5 g (6.82 mmoles) of 1-dimethylaminomethyl-6-methoxy-1,2,3,4-tetrahydroisoquinoline, 1.7 g (8.33 mmoles) of 3,4-dichlorophenylacetic acid and 2.8 g (13.65 mmoles) of dicyclohexylcarbodiimide in 50 ml of dry chloroform.

The silica gel chromatographic column was eluted with hexane, containing increasing amounts of ethyl acetate (5-65%), to afford 1.8 g of the free base which was dissolved in 40 ml of ethyl acetate and the solution brought to acidic pH with HCl/diethyl ether.

The precipitate was filtered, washed and dried, to yield 1.4 g of the title compound.

$C_{21}H_{24}Cl_2N_2O_2.HCl$

M.P.=239°-240° C.

M.W.=443.797

Elemental analysis: Calcd. C,56.83; H,5.68; N,6.31; Cl,23.97 Found C,56.69; H,5.69; N,6.26; Cl,24.00

I.R. (KBr): 1635 (s); 1610 (m); 1505 (m); 1470 (s); 1235 (s) cm$^{-1}$

EXAMPLE 15

1-dimethylaminomethyl-2-(3,4-dichlorophenyl)acetyl-6-chloro-1,2,3,4-tetrahydroisoquinoline hydrochloride.

Prepared as Ex. No. 1, from 1.3 g (5.79 mmoles) of 1-dimethylaminomethyl-6-chloro-1,2,3,4-tetrahydroisoquinoline, 1.4 g (6.86 mmoles) of 3,4-dichlorophenylacetic acid and 2.4 g (11.70 mmoles) of dicyclohexylcarbodiimide in 50 ml of dry chloroform.

The silica gel chromatographic column was eluted with hexane, containing increasing amounts of ethyl acetate (5-65%), to afford 2.0 g of the free base which was dissolved in 40 ml of acetone and the solution brought to acidic pH with HCl/diethyl ether.

The precipitate was filtered, washed and dried, to yield 1.7 g of the title compound.

$C_{20}H_{21}Cl_3N_2O.HCl$

M.P.=241°-242° C.

M.W.=448.220

Elemental analysis: Calcd. C,53.59; H,4.95; N,6.25; Cl,31.64 Found C,53.34; H,4.94; N,6.13; Cl,31.10

I.R. (KBr): 1650 (s); 1445 (s) cm$^{-1}$

EXAMPLE 16

1-(pyrrolidin-1-yl)methyl-2-(3,4-dichlorophenyl)acetyl-6-hydroxy-1,2,3,4-tetrahydroisoquinoline.

Prepared as Ex. No. 5, from 6 g (15.23 mmoles) of 1-(pyrrolidin-1-yl)methyl-6-hydroxy-1,2,3,4-tetrahydroisoquinoline dihydrobromide, 4.1 g (20.0 mmoles) of 3,4-dichlorophenylacetic acid, 5.4 ml (38.42 mmoles) of triethylamine and 6.2 g (30.24 mmoles) of dicyclohexylcarbodiimide in 145 ml of dry chloroform.

The working up of the reaction mixture and the chromatographic column of the crude product were carried out in the same manner described in Ex. No. 5.

2.0 g of the product were obtained and crystallized, as free base, from 95% EtOH, to yield 1.5 g of the title compound.

$C_{22}H_{24}Cl_1N_2O_2$

M.P.=207208° C.

M.W.=419.342

Elemental analysis: Calcd. C,63.00; H,5.77; N,6.68; Cl,16.91 Found C,62.84; H,5.89; N,6.60; Cl,16.84

I.R. (KBr): 3310 (Broad); 1630 (s); 1600 (m); 1435 (m); 1230 (m) cm$^{-1}$

EXAMPLE 17

1-(pyrrolidin-1-yl)methyl-2-(3,4-dichlorophenyl)acetyl-6-methoxy-1,2,3,4-tetrahydroisoquinoline hydrochloride.

Prepared as Ex. No. 1, from 1.5 g (6.09 mmoles) of 1-(pyrrolidin-1-yl)methyl-6-methoxy-1,2,3,4-tetrahydroisoquinoline, 1.5 g (7.35 mmoles) of 3,4-dichlorophenylacetic acid and 2.5 g (12.19 mmoles) of dicyclohexylcarbodiimide in 50 ml of dry chloroform.

The silica gel chromatographic column was eluted with hexane, containing increasing amounts of ethyl acetate (5-65%), to afford 2.1 g of the free base, which was dissolved in 50 ml of ethyl acetate and the solution brought to acidic pH with HCl/diethyl ether.

The precipitate was filtered, washed and dried, to yield 1.8 g of the title compound.

$C_{23}H_{26}Cl_1N_2O_2.HCl$

M.P.=196°-198° C.

M.W.=469.833

Elemental analysis: Calcd. C,58.80; H,5.80; N,5.96; Cl,22.64 Found C,58.90; H,5.84; N,5.93; Cl,22.62

I.R. (KBr): 1630 (s); 1610 (m) cm$^{-1}$

N.M.R. (CDCl$_3$) 300 Mhz: δ 11.71 (s, 1H); 7.20-7.45 (m, 3H); 6.97 (d, 1H); 6.75 (dd, 1H); 6.65 (d, 1H); 6.01 (dd, 1H); 4.23 (m, 1H); 4.07 (m, 1H); 4.05 (AB system, 2H); 3.99 (m, 1H); 3.77 (s, 3H); 3.70 (m, 1H); 3.63 (m, 1H); 3.03 (m, 1H); 2.89 (m, 1H); 2.76 (m, 3H); 2.25 (m, 2H); 2.04 (m, 2H).

EXAMPLE 18

1-(pyrrolidin-1-yl)methyl-2-(3,4-dichlorophenyl)acetyl-6-chloro-1,2,3,4-tetrahydroisoquinoline hydrochloride.

Prepared as Ex. No. 1, from 1.3 g (5.19 mmoles) of 1-(pyrrolidin-1-yl)methyl-6-chloro-1,2,3,4-tetrahydroisoquinoline, 1.3 g (6.37 mmoles) of 3,4-dichlorophenylacetic acid and 2.2 g (10.73 mmoles) of dicyclohexylcarbodiimide in 50 ml of dry chloroform.

The silica gel chromatographic column was eluted with hexane, containing increasing amounts of ethyl acetate (5-65%), to afford 1.5 g of the free base, which was dissolved in 40 ml of acetone and the solution brought to acidic pH with HCl/diethyl ether.

The precipitate was filtered, washed and dried, to yield 700 mg of the title compound.

$C_{22}H_{23}Cl_3N_2O.HCl$

M.P.=222°-224° C.

M.W.=474.256

Elemental analysis: Calcd. C,55.71; H,5.10; N,5.91; Cl,29.91 Found C,55.76; H,5.12; N,5.87; Cl,29.80

I.R. (KBr): 1630 (s); 1425 (m) cm$^{-1}$

EXAMPLE 19

1-(pyrrolidin-1-yl)methyl-2-(3,4-dichlorophenyl)acetyl-7-hydroxy-1,2,3,4-tetrahydroisoquinoline Prepared as Ex. No. 5, from 3 g (7.61 mmoles) of 1-(pyrrolidin-1-yl)methyl-7-hydroxy-1,2,3,4-tetrahydroisoquinoline dihydrobromide, 1.9 g (9.31 mmoles) of 3,4-dichlorophenylacetic acid, 2.3 ml (16.36 mmoles) of triethylamine and 3.2 g (15.61 mmoles) of dicyclohexylcarbodiimide in 110 ml of dry chloroform.

The working up of the reaction mixture and the chromatographic column of the crude product were carried out in the same manner described in Ex. No. 5.

1.0 g of the product was obtained and crystallized, as free base, from ethyl acetate, to yield 700 mg of the title compound.

$C_{22}H_{24}Cl_2N_2O_2$

M.P. = 147°–149° C.

M.W. = 419.342

Elemental analysis: Calcd. C,63.00; H,5.77; N,6.68; Cl,16.91; Found C,62.61; H,5.75; N,6.50; Cl,17.19.

I.R. (KBr): 3410 (broad); 1640 (s); 1450 (s); 1300 (m); 1260 (m) cm$^{-1}$

EXAMPLE 20

1-(pyrrolidin-1-yl)methyl-2-(3,4-dichlorophenyl)acetyl-7-methoxy-1,2,3,4-tetrahydroisoquinoline hydrochloride emihydrate.

Prepared as Ex. No. 1, from 1 g (4.00 mmoles) of 1-(pyrrolidin-1-yl)methyl-7-methoxy-1,2,3,4-tetrahydroisoquinoline, 1.1 g (5.39 mmoles) of 3,4-dichlorophenylacetic acid and 1.4 g (6.83 mmoles) of dicyclohexylcarbodiimide in 50 ml of dry methylene chloride.

The silica gel chromatographic column was eluted with $CH_2Cl_2$, containing increasing amounts of MeOH (0.2–1%), to afford 1.5 g of the product, which was dissolved in 40 ml of ethyl acetate and the solution brought to acidic pH with HCl/diethyl ether.

The precipitate was filtered, washed and dried, to yield 1.3 g of the title compound.

$C_{23}H_{26}Cl_2N_2O_2.HCl.\frac{1}{2}H_2O$

M.P. = 110°–111° C.

M.W. = 478.841

Elemental analysis: Calcd. C,57.68; H,5.89; N,5.85; Cl,22.21 Found C,57.43; H,5.95; N,5.81; Cl,21.99

I.R. (KBr): 1630 (s) cm$^{-1}$

EXAMPLE 21

1-(pyrrolidin-1-yl)methyl-2-(3,4-dichlorophenyl)acetyl-7-chloro-1,2,3,4-tetrahydroisoquinoline hydrochloride Prepared as Ex. No. 1, from 1 g (3.99 mmoles) of 1-(pyrrolidin-1-yl)methyl-7-chloro-1,2,3,4-tetrahydroisoquinoline, 1 g (4.90 mmoles) of 3,4-dichlorophenylacetic acid and 1.7 g (8.30 mmoles) of dicyclohexylcarbodiimide in 50 ml of dry methylene chloride.

The silica gel chromatographic column was eluted with $CH_2Cl_2$, containing increasing amounts of MeOH (0.5–1.5%), to afford 1.8 g of the product, which was dissolved in 50 ml of ethyl acetate and the solution brought to acidic pH with HCl/diethyl ether.

The precipitate was filtered, washed and dried, to yield 1.3 g of the title compound.

Elemental analysis: Calcd. C,60.72; H,5.82; N,6.74; Cl,17.07; Found C,60.32; H,5.76; N,6.73; Cl,17.19.

I.R. (KBr): 3410 (broad); 1640 (s); 1445 (s); 1260 (s) cm$^{-1}$

N.M.R. (CDCl$_3$) 80 Mhz: δ 6.4–7.4 (m, 6H); 5.7 (dd, 1H); 3.2–4.2 (m, 4H); 2.2–3.1 (m, 4H); 2.3 (s, 6H)

EXAMPLE 22

1-dimethylaminomethyl-2-(3,4-dichlorophenyl)acetyl-7-methoxy-1,2,3,4-tetrahydroisoquinoline hydrochloride Prepared as Ex. No. 1, from 1 g (4.54 mmoles) of 1-dimethylaminomethyl-7-methoxy-1,2,3,4-tetrahydroisoquinoline, 1.05 g (5.15 mmoles) of 3,4-dichlorophenylacetic acid and 1.40 g (6.80 mmoles) of dicyclohexylcarbodiimide, in 50 ml of dry methylene chloride.

The silica gel chromatography column was eluted with $CH_2Cl_2$, containing increasing amounts of MeOH (0.2–0.8%), to afford 1.7 g of the product, which was dissolved in 40 ml of ethyl acetate and the solution brought to acidic pH with HCl/diethyl ether.

The precipitate was filtered, washed and dried, to yield 1.5 g of the title compound.

$C_{21}H_{24}Cl_1N_2O_2.HCl$

M.P. = 209°–211° C.

M.W. = 443.797

Elemental analysis: Calcd. C,56.83; H,5.68; N,6.31; Cl,23.97; Found C,56.89; H,5.77; N,6.18; Cl,23.56.

I.R. (KBr): 1630 (s); 1615 (m) cm$^{-1}$ $C_{22}H_{23}Cl_3N_2O.HCl$

M.P. = 275°–278° C.

M.W. = 474.256

Elemental analysis: Calcd. C,55.71; H,5.10; N,5.91; Cl,29.91 Found C,55.73; H,5.05; N,5.88; Cl,29.74

I.R. (KBr): 1635 (s); 1430 (m) cm$^{-1}$

N.M.R. (CD$_3$OD+DMSO) 80 Mhz: δ7.1–7.5 (m, 6H); 6.0 (dd, 1H); 2.6–4.2 (m, 12H); 1.9–2.2 (m, 4H).

EXAMPLE 23

1-dimethylaminomethyl-2-(3,4-dichlorophenyl)acetyl-7-hydroxy-1,2,3,4-tetrahydroisoquinoline ¼ethyl acetate Prepared as Ex. No. 5, from 3 g (8.10 mmoles) of 1-dimethylaminomethyl-7-hydroxy-1,2,3,4-tetrahydroisoquinoline dihydrobromide, 2 g (9.80 mmoles) of 3,4-dichlorophenylacetic acid, 2.5 ml (17.78 mmoles) of triethylamine and 3.3 g (16.10 mmoles) of dicyclohexylcarbodiimide, in 110 ml of dry chloroform.

The working up of the reaction mixture and the chromatographic column of the crude product were carried out in the same manner described in Ex. No. 5.

1.4 g of the product were obtained and crystallized, as free base, from ethyl acetate, to yield 1.2 g of the title compound.

$C_{22}H_{23}Cl_3N_2O.HCl$

M.P. = 129°–131° C.

M.W. = 415.332

EXAMPLE 24

1-dimethylaminomethyl-2-(3,4-dichlorophenyl)acetyl-7-chloro-1,2,3,4-tetrahydroisoquinoline hydrochloride ⅓ethanol.

Prepared as Ex. No. 1, from 1 g (4.45 mmoles) of 1-dimethylaminomethyl-7-chloro-1,2,3,4-tetrahydroisoquinoline, 1.1 g (5.40 mmoles) of 3,4-dichlorophenylacetic acid and 1.9 g (9.22 mmoles) of dicyclohexylcarbodiimide, in 50 ml of dry methylene chloride.

The day after dicyclohexylurea was filtered off and the solution evaporated in vacuo to dryness.

The residue was treated with 50 ml of 8% HCl solution and 50 ml of ethyl acetate at 60° C., 1 hour.

The precipitate was filtered and crystallized twice from absolute EtOH, to yield 1 g of the title compound.
$C_{20}H_{21}Cl_3N_2O\cdot HCl\cdot\frac{1}{2}EtOH$

M.P.=258°-260° C.
M.W.=463.576

Elemental analysis : Calcd. C,53.54; H,5.22; N,6.04; Cl,30.60; Found C,53.15; H,5.21; N,5.97; Cl,30.35.

I.R. (KBr): 1645 (s); 1445 (m) cm$^{-1}$

N.M.R. (CD$_3$OD+DMSO)80 Mhz: 7.1 .7.5 (m, 6H); 6.0 (dd, 1H); 2.7 -4.2 (m, 8H); 3.0 (s, 6H).

EXAMPLE 25

1-(pyrrolidin-1-yl)methyl-2-(3,4-dichlorophenyl)acetyl-8-hydroxy-1,2,3,4-tetrahydroisoquinoline Prepared as Ex. No. 5, from 13.2 g (33.50 mmoles) of a mixture containing 1-(pyrrolidin-1-yl)methyl-8-hydroxy-1,2,3,4-tetrahydroisoquinoline dihydrobromide and 1-(pyrrolidin-1-yl)methyl-6-hydroxy-1,2,3,4-tetrahydroisoquinoline dihydrobromide, 9.6 g (46.8 mmoles) of 3,4-dichlorophenylacetic acid, 14 ml (99.6 mmoles) of triethylamine and 17 g (82.52 mmoles) of dicyclohexylcarbodiimide, in 280 ml of dry chloroform.

The working up of the reaction mixture was carried out in the same manner described in Ex. No. 5; the silica gel chromatographic column was eluted with CH$_2$Cl$_2$, containing increasing amounts of MeOH (0.2–0.8%), to afford 1.2 g of the least polar product, which was crystallized from 40 ml of ethyl acetate to give 0.9 g of the title compound.
$C_{22}H_{24}Cl_2N_2O_2$

M.P.=151°-153° C.
M.W.=419.342

Elemental analysis: Calcd. C, 63.00; H, 5.77; N, 6.68 Found C, 63.01; H, 5.68; N, 6.64

I.R. (KBr): 3420 (broad); 2500 (broad); 1645 (s); 1430 (m) cm$^{-1}$

EXAMPLE 26

1-(pyrrolidin-1-yl)methyl-2-(3,4-dichlorophenyl)acetyl-8-methoxy-1,2,3,4-tetrahydroisoquinoline hydrochloride Prepared as Ex. No. 1, from 4.3 g (17.48 mmoles) of a mixture containing 1-(pyrrolidin-1-yl)methyl-8-methoxy-1,2,3,4-tetrahydroisoquinoline and 1-(pyrrolidin-1-yl)methyl-6-methoxy-1,2,3,4-tetrahydroisoquinoline, 4.3 g (20.98 mmoles) of 3,4-dichlorophenylacetic acid, and 8.0 g (38.80 mmoles) of dicyclohexylcarbodiimide, in 110 ml of dry methylene chloride. The silica gel chromatographic column was eluted with CH$_2$Cl$_2$, containing increasing amounts of MeOH (0.6–2.5%); 1.5 g of the crude product were obtained and dissolved in 40 ml of ethyl acetate. The solution was brought to acidic pH with HCl/diethyl ehter and the precipitate filtered, washed and dried, to yield 1.2 g of the title compound.
$C_{23}H_{26}Cl_2N_2O_2\cdot HCl$

M.P.=248°-250° C.
M.W.=469.833

Elemental analysis: Calcd. C, 58.80; H, 5.80; N, 5.96 Found C, 58.53; H, 5.81; N, 5.80

I.R. (KBr): 1630 (s); 1470 (m) cm$^{-1}$

N.M.R. (CDCl$_3$)300 Mhz: δ11.52 (s, 1H); 7.20–7.45 (m, 4H) 6.75 (m, 2H); 6.23 (m, 1H); 4.24 (m, 1H); 4.14 (m, 1H); 4.05 (AB system, 2H); 3.99 (m, 1H); 3.85 (s, 3H); 3.72 (m, 1H); 3.52 (m, 1H); 3.11 (m, 2H); 2.76 (m, 3H); 2.26 (m, 2H); 2.02 (m, 2H).

EXAMPLE 27

1-(pyrrolidin-1-yl)methyl-2-(3,4-dichlorophenyl)acetyl-8-chloro-1,2,3,4-tetrahydroisoquinoline hydrochloride ½hydrate 1.9 g (7.58 mmoles) of a mixture containing 1-(1-pyrrolidinylmethyl)-6-chloro-1,2,3,4-tetrahydroisoquinoline and 1-(1-pyrrolidinylmethyl)-8-chloro-1,2,3,4-tetrahydroisoquinoline, were dissolved in 50 ml of dry methylene chloride and 1.9 g (9.26 mmoles) of 3,4-dichlorophenylacetic acid were added.

3.2 g (15.53 mmoles) of dicyclohexylcarbodiimide, dissolved in 10 ml of dry methylene chloride, were added dropwise to this solution, at −5° C.

The reaction mixture was allowed to reach room temperature, stirred 6 hours and left overnight.

The precipitated dicyclohexylurea was filtered off and the solution was evaporated in vacuo to dryness.

The residual oil was chromatographed on silica gel, eluting with CH$_2$Cl$_2$, containing increasing amounts of MeOH (0.2–0.6%), to afford 1.5 g of the least polar product, which was dissolved in 70 ml of acetone and the solution brought to acidic pH with HCl/diethyl ether. The precipitate was filtered, washed and dried, to yield 1.2 g of a compound which, by comparison with an authentic sample, was identified as 1-(1-pyrrolidinyl-methyl)-2-(3,4-dichlorophenylacetyl)-6-chloro-1,2,3,4-tetrahydroisoquinoline hydrochloride.
$C_{22}H_{23}Cl_3N_2O\cdot HCl$

M.P.=222°-224° C.
M.W.=474.256

Elemental analysis: Calcd. C, 55.71; H, 5.10; N, 5.91; Cl, 29.91 Found C, 55.76; H, 5.12; N, 5.87; Cl, 29.80

I.R. (KBr): 1630 cm$^{-1}$ (s)

Continuing the elution of the chromatographic column with an increased amount of MeOH (0.6–2.5%), 300 mg of a second product were obtained.

This was dissolved in 20 ml of acetone and the solution brought to acidic pH with HCl/diethyl ether. The precipitate was filtered, washed and dried, to yield 200 mg of the title compound.
$C_{22}H_{23}Cl_3N_2O\cdot HCl\cdot\frac{1}{2}H_2O$

M.P.=231°-234° C.
M.W.=478.760

Elemental analysis: Calcd. C, 55.19; H, 5.16; N, 5.85; Found C, 55.07; H, 4.93; N, 5.76.

I.R. (KBr) : 1645 cm (s); 1445 cm$^{-1}$ (s).

EXAMPLE 28 b 1-(pyrrolidin-1-yl)eth-1-yl-2-(3,4-dichlorophenyl)acetyl-1,2,3,4-tetrahydroisoquinoline. Diastereoisomer A Prepared as Ex. No. 1, from 4 g (17.39 mmoles) of 1-(pyrrolidin-1-yl)eth-1-yl-1,2,3,4-tetrahydroisoquinoline (diastereoisomeric mixture), 4 g (19.60 mmoles) of 3,4-dichlorophenylacetic acid and 5.5 g (26.70 mmoles) of dicyclohexylcarbodiimide, in 100 ml of dry methylene chloride.

The silica gel chromatographic column was eluted with hexane, containing increasing amounts of ethyl acetate (10–25%), to afford 4.5 g of a diastereoisomeric mixture. Treatment with 250 ml of hot MeOH induced the crystallization of the least soluble product which was recrystallized from MeOH/H$_2$O, to yield 1.6 g of the title compound.
$C_{23}H_{26}Cl_2N_2O$

M.P.=148°-150° C.

M.W.=417.368

Elemental analysis: Calcd. C,66.18; H,6.28; N,6.71; Cl,16.99 Found C,65.83; H,6.30; N,6.62; Cl,17.12

I.R. (KBr) : 1630 (s); 1445 (m) cm$^{-1}$

N.M.R. (CDCl$_3$)300 Mhz (64.35 thautomeric amides mixture): $\delta$7.00–7.40 (m, 7H); 5.51 (d, 0.65H); 4.68 (m, 0.65H); 2.45–3.85 (m, 10.7H); 1.55–1.78 (m, 4H); 0.90–1.00 (2d, 3H).

EXAMPLE 29

1-(pyrrolidin-1-yl)eth-1-yl-2-(3,4-dichlorophenyl)acetyl-1,2,3,4-tetrahydroisoquinoline. Diastereoisomer B.

The methanolic solution of the mother liquor of the previous compound was cooled overnight at 0°–4° C.; the precipitate was collected and crystallized twice from MeOH to yield 0.7 g of the title compound.

$C_{23}H_{26}Cl_2N_2O$

M.P.=108°–110° C.

M.W.=417.368

Elemental analysis: Calcd. C,66.18; H,6.28; N,6.71; Cl,16.99 Found C,66.04; H,6.20; N,6.76; Cl,16.89

I.R. (KBr) : 1630 (s); 1465 (m) cm$^{-1}$ 6.90–7.45(m, 7H); 5.60 (d, 1H);

N.M.R. (CDCl$_3$) $\delta$ (m, 11H); 1.60–1.85 (m, 4H); 2.20–4.65 (m, 11H); 1.60–1.85 (m, 4H); 1.08 (d, 3H).

EXAMPLE 30

1-dimethylamino-eth-1-yl-2-(3,4-dichlorophenyl)acetyl-1,2,3,4 -tetrahydroisoquinoline. Diastereoisomer A - Erithro form.

Prepared as Ex. No. 1, from 2.7 g (13.30 mmoles) of 1- dimethylamino-eth-1-yl-1,2,3,4-tetrahydroisoquinoline (diastereoisomeric mixture), 3.05 g (15.00 mmoles) of 3,4-dichlorophenylacetic acid and 4.2 g (20.39 mmoles) of dicyclohexylcarbodiimide, in 100 ml of dry methylene chloride.

The silica gel chromatographic column was eluted with hexane, containing increasing amounts of ethyl acetate (5–10%), to afford 1 g of the least polar product which was crystallized from MeOH to yield 0.7 g of the title compound.

$C_{21}H_{24}Cl_2N_2O$

M.P.=143°–144° C.

M.W.=391.332

I.R. (KBr) : 1630 (s); 1400 (m) cm$^{-1}$

N.M.R. (CDCl$_3$) $\delta$7.00–7.45 (m 7H); 5.42 (d, 0.75H); 4.60–4.70 (m, 0.25H); 4.55 (d, 0.25H); (75:25 thautomeric 3.70–3.80 (m, 3H); 3.50–3.61 (m, 0.75H); 2.75–3.10 (m, 3H); 2.2 (2s, 6H); 0.90 (2d, 3H).

EXAMPLE 31

1-dimethylamino-eth-1-yl-2-(3,4-dichlorophenyl)acetyl-1,2,3,4-tetrahydroisoquinoline. Diastereoisomer B - threo form.

Continuing the elution of the chromatographic column described for the previous compound with an increased amount of ethyl acetate (10–30%) 2.4 g of a second product were obtained and crystallized from MeOH, to yield 2.2 g of the title compound.

$C_{21}H_{24}Cl_2N_2O$

M.P.=124°–126° C.

M.W.=391.332

Elemental analysis: Calcd. C,64.45; H,6.18; N,7.16; Cl,18.12 Found C,64.25; H,6.24; N,7.04; Cl,17.98

I.R. (KBr) : 1630 (s); 1470 (m) cm$^{-1}$

N.M.R. (CDCl$_3$) 6.85–7.50 (m, 7H); 5.50 (d, 0.82H); 270 Mhz 4.50 (d, 0.18H); 4.38 (m, 0.18H); (82:18 thautomeric 3.40–3.90 (m, 3.82H); 2.73–3.00 (m, 3H); 2.25 (2s, 6H); 0.97 (d, 2.46H); 0.75 (d, 0.54H).

EXAMPLE 32

1-(pyrrolidin-1-yl)methyl-2-(3,4-dichlorophenyl)acetyl-5-methylthio-1,2,3,4-tetrahydroisoquinoline hydrochloride Prepared as Ex. No. 1, from 1.4 g (5.34 mmoles) of 1-(pyrrolidin-1-yl)methyl-5-methylthio-1,2,3,4-tetrahydroisoquinoline, 1.3 g (6.37 mmoles) of 3,4dichlorophenylacetic acid and 2.6 g (12.74 mmoles) of dicyclohexylcarbodiimide in 50 ml of dry chloroform. The silica gel chromatographic column was eluted with $CH_2Cl_2$, containing increasing amounts of MeOH (0.2–1%), to afford 800 mg of the free base, which was dissolved in ethyl acetate and the solution brought to acidic pH with HCl/diethyl ether. The precipitate was filtered, washed and dried, to yield 500 mg of the title compound.

$C_{23}H_{26}Cl_2N_2OS.HCl$

M.P.=171° C.

M.W.=485.899

I.R. (KBr) : 1640 (s) cm$^{-1}$

N.M.R. (CDCl$_3$), : $\delta$11.40 (s broad, 1H); 6.85–7.50 (m, 6H); 6.10 (d broad, 1H); 3.45–4.45 (m, 6H); 1.85–3.25 (m, 13H).

EXAMPLE 33

1-(pyrrolidin-1-yl)methyl-2-(4-trifluoromethylphenyl)acetyl5-methoxy-1,2,3,4-tetrahydroisoquinoline hydrochloride 750 mg (3.05 mmoles) of 1-(pyrrolidin-1-yl)methyl-5-methoxy1,2,3,4-tetrahydroisoquinoline were dissolved in 10 ml of dry chloroform. 810 mg (3.64 mmoles) of 4-trifluoromethylphenyl acetyl chloride, dissolved in 10 ml of chloroform, were added dropwise to the solution at 0° C. The reaction mixture was allowed to reach room temperature and left overnight.

The solvent was evaporated in vacuo to dryness and the residue was crystallized from 40 ml of acetone to yield 1.2 g of the title compound.

$C_{24}H_{27}F_3N_2O_2.HCl$

M.P.=236°–238° C.

M.W.=468.937

Elemental analysis: Calcd. C, 61.47; H, 6.02; N, 5.97; Found C, 61.58; H, 6.19; N, 5.91.

I.R. (KBr) 1630 (s) cm$^{-1}$

EXAMPLE 34

1-(pyrrolidin-1-yl)methyl-2-(4-trifluoromethylphenyl)acetyl5-hydroxy-1,2,3,4-tetrahydroisoquinoline hydrochloride hemihydrate 1.8 g (4.57 mmoles) of 1-(pyrrolidin-1-yl)methyl-5-hydroxy1,2,3,4-tetrahydroisoquinoline dihydrobromide and 2.7 ml (19.23 mmoles) of Et$_3$N were dissolved in 50 ml of dry chloroform and the solution cooled at -10° C. 2.24 g (10.06 mmoles) of 4-trifluoromethylphenyl acetyl chloride, dissolved in 10 ml of chloroform, were added portionwise and the reaction mixture was allowed to reach room temperature and left overnight.

The solvent was evaporated in vacuo to dryness and the residue was treated with 100 ml of 8% HCl and 30 ml of ethanol, one hour at 80° C. The solution was evaporated in vacuo to dryness and the residual oil was treated with acq. NH$_3$ solution and exhaustively extracted with ethyl acetate. The organic layer was dried over Na2S04 and concentrated in vacuo to dryness.

The residue was chromatographed on silica gel, eluting with CH$_2$Cl$_2$, containing increasing amounts of MeOH (0.5–3.5%), to afford 530 mg of the free base, which was dissolved in 25 ml of ethyl acetate and the solution brought to acidic pH with HCl/diethyl ether.

The precipitate was filtered, washed and dried, to yield 500 mg of the title compound.

C$_{23}$H$_{25}$F$_3$N$_2$O$_2$.HCl.1/2 H$_2$O

M.P.=164–66° C.
M.W.=463.919

Elemental analysis: Calcd. C, 59.54; H, 5.86; N, 6.04; Found C, 59.84; H, 5.71; N, 6.04.

I.R. (KBr) : 3400,3200 (broad), 1640 (s), 1590 (m), 1325 (s) cm$^{-1}$.

EXAMPLE 35

1-(piperidin-1-yl)methyl-2-(4-trifluoromethylphenyl)acetyl5-methoxy-1,2,3,4-tetrahydroisoquinoline hydrochloride Prepared as Ex. No. 33, from 600 mg (2.31 mmoles) of 1-(piperidin-1-yl)methyl-5-methoxy-1,2,3,4-tetrahydroisoquinoline and 630 mg (2.83 mmoles) of 4-trifluoromethylphenyl acetyl chloride in 20 ml of dry chloroform.

The crude product was crystallized from 30 ml of a acetone/ethyl acetate mixture, to yield 1.0 g of the title compound.

C$_{25}$H$_{29}$F$_3$N$_2$O$_2$ HCl

M.P.=231°–233° C.
M.W.=482.963

Elemental analysis: Calcd. C, 62.17; H, 6.26; N, 5.80; Found C, 61.71; H, 6.39; N, 5.69.

I.R. (KBr) : 1635 (s) cm$^{-1}$

EXAMPLE 36

1-(piperidin-1-yl)methyl-2-(3,4-dichlorophenyl)acetyl-5-methoxy-1,2,3,4-tetrahydroisoquinoline hydrochloride Prepared as Ex. No. 33, from 600 mg (2.31 mmoles) of 1-(piperidin-1-yl)methyl-5-methoxy-1,2,3,4-tetrahydroisoquinoline and 630 mg (2.82 mmoles) of 3,4-dichlorophenyl acetyl chloride in 20 ml of dry chloroform.

The crude product was crystallized from 30 ml of acetone, to yield 970 mg of the title compound.

C$_{24}$H$_{28}$Cl$_2$N$_2$O$_2$. HCl

M.P.=238°–240° C.
M.W.=483.859

Elemental analysis: Calcd. C, 59.57; H, 6.04; N, 5.79; Found C, 59.72; H, 6.09; N, 5.70.

I.R. (KBr) : 1640 (s) cm$^{-1}$

EXAMPLE 37

1-(piperidin-1-yl)methyl-2-(4-trifluoromethylphenyl)acetyl5-hydroxy-1,2,3,4-tetrahydroisoquinoline hydrochloride Prepared as Ex. No. 34, from 1.65 g (4.06 mmoles) of 1-(piperidin-1-yl)methyl-5-hydroxy-1,2,3,4-tetrahydroisoquinoline dihydrobromide, 2.6 ml (18.50 mmoles) of Et3N and 2.2 g (9.89 mmoles) of 4-trifluoromethylphenyl acetyl chloride in 30 ml of dry chloroform.

The work up of the reaction mixture and the chromatographic column of the crude product were carried out in the same manner described in Ex. No. 34.

900 mg of the title compound were crystallized from ethyl acetate.

C$_{24}$H$_{27}$F$_3$N$_2$O$_2$. HCl

M.P.=168° C.
M.W.=468.937

Elemental analysis: Calcd. C, 61.47; H, 6.02; N, 5.97; Found C, 61.26; H, 6.00; N, 5.92.

I.R. (KBr) : 3190,3400 (broad), 1650 (s), 1590 (m), 1325 (s) cm$^{-1}$.

EXAMPLE 38

1-(piperidin-1-yl)methyl-2-(3,4-dichlorophenyl)acetyl-5-hydroxy-1,2,3,4-tetrahydroisoquinoline hydrochloride Prepared as Ex. No. 34, from 1.65 g (4.06 mmoles) of 1-(piperidin-1-yl)methyl-5-hydroxy-1,2,3,4-tetrahydroisoquinoline dihydrobromide, 2.6 ml (18.50 mmoles) of Et3N and 2.2 g (9.84 mmoles) of 3,4-dichlorophenyl acetyl chloride in 50 ml of dry chloroform.

The work up of the reaction mixture and the chromatographic column of the crude product were carried out in the same manner described in Ex. No. 34.

1.4 g of the title compound were crystallized from ethyl acetate.

C$_{2}$H$_{26}$Cl$_2$N$_2$O$_2$.HCl

M.P.=170° C.
M.W.=469.833

I.R. (KBr}: 3180,3420 (broad), 1640 (s), 1590 (m), 1420 (m), 1280 (m) cm$^{-1}$.

EXAMPLE 39

1-(pyrrolidin-1-yl)methyl-2-(3,4-dichlorophenyl)acetyl-5,6-dimethoxy-1,2,3,4-tetrahydroisoquinoline hydrochloride Prepared as Ex. No. 33, from 1.3 g (4.71 mmoles) of 1-(pyrrolidin-1-yl)methyl-5,6-dimethoxy-1,2,3,4-tetrahydroisoquinoline and 1.1 g (4.92 mmoles) of 3,4-dichlorophenyl acetyl chloride in 40 ml of dry chloroform. The crude product was crystallized from 40 ml of ethyl acetate, to yield 1.3 g of the title compound.

C$_{24}$H$_{28}$Cl$_2$N$_2$O$_3$.HCl

M.P.=232°–235° C.
M.W.=499.859

Elemental analysis: Calcd. C, 57.66; H, 5.85; N, 5.60 Found C, 57.57; H, 5.80; N, 5.63.

I.R. (KBr) : 1630 (s), 1495 (m), 1280 (m) cm$^{-1}$.

EXAMPLE 40

1-(pyrrolidin-1-yl)methyl-2-(3,4-dichlorophenyl)acetyl-5,6-dihydroxy-1,2,3,4-tetrahydroisoquinoline hydrochloride Prepared as Ex. No. 5, from 16.0 g (39.04 mmoles) of 1-(pyrrolidin-1-yl)methyl-5,6-dihydroxy-1,2,3,4-tetrahydroisoquinoline dihydrobromide, 12.5 g (60.98 mmoles) of 3,4dichlorophenyl acetic acid, 16 ml (110 mmoles) of Et3N and 18.0 g (88.23 mmoles) of dicyclohexylcarbodiimide in 270 ml of dry chloroform.

The work up of the reaction mixture was carried out in the same manner described in Ex. No. 5.

The silica gel chromatographic column was eluted with CH$_2$Cl$_2$, containing increasing amounts of MeOH (1–20 %) and 32% NH$_4$OH (0.5–2%), to afford 2.9 g of the free base, which was dissolved in 70 ml of acetone and the solution brought to acidic pH with HCl/diethyl ether.

The precipitate was filtered, washed and dried, to yield 2.1 g of the title compound.

C$_{22}$H$_{24}$Cl$_2$N$_2$O$_3$.HCl

M.P.=241°-243° C.
M.W.=471.807

Elemental analysis : Calcd. C, 56.00; H, 5.34; N, 5.94; Found C, 55.72; H, 5.43; N, 5.92.

I.R. (KBr) : 3250,3420 (broad), 1640 (s), 1450 (m) cm$^{-1}$

N.M.R. (MeOD+D$_2$O) : δ6.45-6.85 (m, 3H); 6.05 (AB system, J=7.5 Hz, 2H); 5.22 (dd, 1H); 1.75-3.60 (m, 12H); 1.30-1.55 (m, 4H).

EXAMPLE 41

(+)-1-(pyrrolidin-1-yl)methyl-2-(3,4-dichlorophenyl)acetyl3-methyl-1,2,3,4-tetrahydroisoquinoline L(+) tartrate 4.2 g (10.06 mmoles) of the compound of the Ex. No. 1 (as free base) were dissolved in 100 ml of abs. ethanol. 1.65 g (10.99 mmoles) of L(+) tartaric acid, dissolved in 80 ml of abs. ethanol, were added to the hot solution of the racemic base.

The mixture was gently warmed for 15' and the least soluble diastereoisomeric salt was allowed to crystallize on standing.

This salt was recrystallized from 95% EtOH up to a constant rotatory power, to yield 2.0 g of the title compound.

C$_{23}$H$_{26}$Cl$_2$N$_2$O . L(+) C$_4$H$_6$O$_6$
M.P.=202° C.
M.W.=567.456
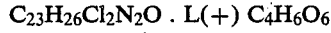 +17.65 (C=1, MeOH)

Elemental analysis: Calcd. C, 57.14; H, 5.68; N, 4.94; Found C, 57.03; H, 5.78; N, 4.89.

80 mg of this compound were treated with NH$_4$OH solution and extracted with diethyl ether, to obtain the free base, which gave an:

$[\alpha]_D^{20}$ 17.38 (C=1, CHCl$_3$)

The I.R. and the N.M.R. spectra were identical to those obtained for the racemate.

EXAMPLE 42

(−)-1-(pyrrolidin-1-yl)methyl-2-(3,4-dichlorophenyl)acetyl-3-methyl-1,2,3,4-tetrahydroisoquinoline D(-) tartrate The mother liquors of the first crystallization of the Ex. No. 41 were treated with NH$_{40}$H solution and exhaustively extracted with diethyl ether, to afford 1.90 g (4.55 mmoles) of the enriched free base, which were dissolved in 60 ml of 95% ethanol.

0.72 g (4.79 mmoles) of D(-) tartaric acid, dissolved in 60 ml of 95% ethanol were added to the hot solution and the diastereoisomeric salt crystallized on standing.

This salt was recrystallized from 95% EtOH up to a constant rotatory power, to yield 1.9 g of the title compound.

C$_{23}$H$_{26}$Cl$_2$N$_2$O . D(−) C$_4$H$_6$O$_6$
M.P.=201°-202° C.
M.W.=567.456
$[\alpha]_D^{20}$=−17.81 (C=1, MeOH)
Elemental analysis: Calcd. C, 57.14; H, 5.68; N, 4.94; Found C, 56.97; H, 5.74; N, 4.88. 80 mg of this compound were treated with NH$_{40}$H solution and extracted with diethyl ether, to obtain the free base, which gave an:

$[\alpha]_D^{20}$=−17.70 (C=1, CHCl$_3$)

The I.R. and the N.M.R. spectra were identical to those obtained for the racemate.

EXAMPLE 43

(+)-1-(pyrrolidin-1-yl)methyl-2-(3,4-dichlorophenyl)acetyl-4-methyl-1,2,3,4-tetrahydroisoquinoline L(+) tartrate 4.4 g (10.54 mmoles) of the compound of the Ex. No. 3 (as free base) were dissolved in 100 ml of acetone.

1.70 g (11.32 mmoles) of L(+) tartaric acid, dissolved in 80 ml of acetone, were added to the hot solution of the racemic base.

The mixture was gently warmed for 15' and the least soluble diastereoisomeric salt crystallized on standing.

This salt was recrystallized from acetone, containing 5% of EtOH, up to a constant rotatory power, to yield 2.2 g of the title compound.

C$_{23}$H$_{26}$Cl$_2$N$_2$O . L(+) C$_4$H$_6$O$_6$
M.P.=185° C.
M.W.=567.456
$[\alpha]_D^{20}$=+23.28 (C=1, MeOH) 75 mg of this compound were treated with NH$_{40}$H solution and extracted with diethyl ether, to obtain the free base, which gave an:
$[\alpha]_D^{20}$=+25.00 (C=1, CHCl$_3$)

The I.R. and the N.M.R. spectra were identical to those obtained for the racemate.

EXAMPLE 44

(−)-1-(pyrrolidin-1-yl)methyl-2-(3,4-dichlorophenyl)acetyl-4-methyl-1,2,3,4-tetrahydroisoquinoline D(-) tartrate The mother liquors of the first crystallization of the Ex. No. 43 were treated with NH$_{40}$H solution and exhaustively extracted with diethyl ether, to afford 2.0 g (4.79 mmoles) of the enriched free base, which were dissolved in 60 ml of acetone.

0.78 g (5.19 mmoles) of D(-) tartaric acid, dissolved in 40 ml of acetone, were added to the hot solution and the diastereoisomeric salt crystallized on standing.

This salt was recrystallized from acetone, containing 5% of EtOH, up to a constant rotatory power, to yield 1.9 g of the title compound.

C$_{23}$H$_{26}$Cl$_2$N$_2$O . D(−) C$_4$H$_6$O$_6$
M.P.=185° C.
M.W.=567.456
$[\alpha]_D^{20}$=−23.76 (C=1, MeOH)

75 mg of this compound were treated with NH$_{40}$H solution and extracted with diethyl ether, to obtain the free base, which gave an:
$[\alpha]$=−25.48 (C=1, CHCl$_3$)
The
I.R. and the N.M.R. spectra were identical to those obtained for the racemate.

EXAMPLE 45

1-(pyrrolidin-1-yl)methyl-2-(3,4-dichlorophenyl)acetyl-3,4-dimethyl-1,2,3,4-tetrahydroisoquinoline diastereoisomer A 3.95 g (16.19 mmoles) of crude 1-(pyrrolidin-1-yl)methyl-3,4-dimethyl-1,2,3,4-tetrahydroisoquinoline (2:1 diastereoisomeric mixture of the diamines synthesized starting from trans-1-chloromethyl-3,4-dimethyl-3,4-dihydroisoquinoline hydrochloride) were dissolved in 60 ml of dry chloroform.

4.5 g (32.60 mmoles) of anhydrous potassium carbonate were added and the solution cooled at −5° C.

4.8 g (21.47 mmoles) of 3,4-dichlorophenylacetyl chloride, dissolved in 20 ml of chloroform, were added dropwise and the solution was allowed to reach room temperature and left overnight.

20 ml of water were added and the biphasic solution stirred for 30'; the organic layer was separated, washed with H$_2$0 and dried over Na$_2$SO$_4$. The solvent was evaporated in vacuo to dryness and the residue was flash chromatographed on 230–400 mesh silica gel, eluting with a mixture of hexane/AcOEt/32% NH$_4$OH solution 35:17:0.07, to afford 3.0 g of the least polar product which was crystallized from 50 ml of methanol, to yield 2.6 g of the title compound.

$C_{24}H_{28}Cl_2N_2O$

M.P.=126°–129° C.

M.W.=431.394

Elemental analysis: Calcd. C,66.82; H,6.54; N,6.49; Cl,16.44; Found C,67.00; H,6.64; N,6.46; Cl,16.32.

I.R. (KBr) 1645 (s), 1390 (s), 760 (s) cm$^{-1}$

N.M.R. (CDCl$_3$) 6.95–7.45 (m, 7H); 4.93 (dd, 1H); 4.08 (dq, 1H); 3.80 (AB system, 2H); 2.25–3.05 (m, 7H); 1.55–1.78 (m, 4H); 1.25 (d, 3H); 0.99 (d, 3H).

EXAMPLE 46

1-(pyrrolidin-1-yl)methyl-2-(3,4-dichlorophenyl)acetyl-3,4-dimethyl-1,2,3,4-tetrahydroisoquinoline diastereoisomer B Continuing the elution of the chromatographic column of the Ex. No. 45, 1.3 g of a second product were obtained and crystallized from 50 ml of hexane to yield 1.0 g of the title compound.

$C_{24}H_{28}Cl_2N_2O$

M.P.=117°–119° C.

M.W.=431.394

Elemental analysis: Calcd. C,66.82; H,6.54; N,6.49; Cl,16.44; Found C,66.75; H,6.56; N,6.47; Cl,16.26.

I.R. (KBr) 1640 (s), 1410 (m), 760 (m) cm$^{-1}$

N.M.R. (CDCl$_3$) : $-\delta$7.75–7.95 (m, 0.65H); 6.85–7.55 (m, 6.35H); 5.60 (dd, 0.65H); 4.65–5.15 (m, 0.65H); 3.45–4.20 (m, 2.35H); 2.30–3.20 (m, 6.70H); 1.55–1.85 (m, 4H); 0.90–1.35 (m, 6.65H).

EXAMPLE 47

1-(pyrrolidin-1-yl)methyl-2-(3,4-dichlorophenyl)acetyl-3,4-dimethyl-1,2,3,4-tetrahydroisoquinoline hydrochloride diastereoisomer C Prepared as Ex. No. 45, from 4.5 g (18.44 mmoles) of crude 1-(pyrrolidin-1-yl)methyl-3,4-dimethyl-1,2,3,4-tetrahydroisoquinoline (synthesized starting from cis-1-chloromethyl-3,4-dimethyl-3,4-dihydroisoquinoline hydrochloride), 5.10 g (36.95 mmoles) of anhydrous potassium carbonate and 5.33 g (23.84 mmoles) of 3,4-dichlorophenylacetyl chloride in 90 ml of dry chloroform. The work up of the reaction mixture was carried out in the same manner described in Ex. No. 45.

The silica gel flash chromatography was performed eluting with a mixture of CH$_2$Cl$_2$ 40 / MeOH 1 / 32% NH$_4$OH solution 0.1, to afford 3.5 g of the free base, which was transformed into the hydrochloride by treatment with HCl/diethyl ether, to yield 3.3 g of the title compound.

$C_{24}H_{28}Cl_2N_2O \cdot HCl$

M.P.=106° C.

M.W.=467.859

I.R. (KBr) : 1645 (s), 1470 (m), 1410 (m) cm$^{-1}$

N.M.R. (CDCl$_3$): $\delta$11.40 (s broad, 1H); 7.00–7.55 (m, 7H); 6.12 (dd, 1H); 2.51–4.51 (m, 10H); 1.70–2.45 (m, 4H); 1.20–1.51 (2d, 6H).

EXAMPLE 48

1-(piperidin-1-yl)methyl-2-(3,4-dichlorophenyl)acetyl-3,4-dimethyl-1,2,4-tetrahydroisoquinoline diastereoisomer A.

Prepared as Ex. No. 45, from 2.34 g (9.07 mmoles) of crude 1-(piperidin-1-yl)methyl-3,4-dimethyl-1,2,3,4-tetrahydroisoquinoline (2:1 distereoisomeric mixture of the diamines synthesized starting from trans-1-chloromethyl-3,4-dimethyl-3,4-dihydroisoquinoline hydrochloride), 2.5 g (18.12 mmoles) of anhydrous potassium carbonate and 2.44 g (10.92 mmoles) of 3,4-dichlorophenyl aceytl chloride in 55 ml of dry chloroform.

The work up of the reaction mixture was carried out as described in Ex. No. 45 and the silica gel flash chromatographic column was eluted with a mixture of hexane/AcOEt/32% NH$_4$OH solution 40:10:0.05, to afford 1.3 g of the least polar product which was crystallized from 30 ml of methanol, to yield 1.1 g of the title compound.

$C_{25}H_{30}Cl_2N_2O$

M.P.=130°–132° C.

M.W.=445.420

Elemental analysis: Calcd. C,67.41; H,6.79; N,6.29; Cl, 15.92; Found C,67.68; H,6.87; N,6.23; Cl, 15.64.

I.R. (KBr) : 1645 (s), 1390 (m) cm$^{-1}$

N.M.R. (CDCl$_3$ ) : $\delta$6.90–7.55 (m, 7H); 4.82 (dd broad, 1H); 4.08 (dq broad, 1H); 3.74 (s, 2H); 2.45–2.92 (m, 4H); 1.85–2.35 (m, 3H); 0.88–1.62 (m, 12H).

EXAMPLE 49

1-(piperidin-1-yl)methyl-2-(3,4-dichlorophenyl)acetyl-3,4-dimethyl-1,2,3,4-tetrahydroisoquinoline diastereoisomer B.

Continuing the elution of the chromatographic column of the Ex. No. 48, 0.8 g of a second product were obtained and crystallized from 20 ml of hexane to yield 0.6 g of the title compound.

$C_{25}H_{30}Cl_2N_2O$

M.P.=136°–137° C.

M.W.=445.420

Elemental analysis: Calcd. C,67.41; H,6.79; N,6.29; Cl, 15.92; Found C,67.70; H,6.83; N,6.25; Cl,15.68.

I.R. (KBr) : 1638 (s), 1470 (m), 1430 (m), 1410 (m) cm$^{-1}$

N.M.R. (CDCl$_3$): 7.80–8.07 (m, 0.63H); 6.90–7.45 (m, 6.37H); 5.57 (dd, 0.63H); 4.90 (dq, 3.65–4.12 (m, 2.74H); 2.20–2.90 (m, 7H); 0.90–1.75 (m, 12H).

EXAMPLE 50

1-(pyrrolidin-1-yl)methyl-2-(3,4-dichlorophenyl)acetyl-4-phenyl-1,2,3,4-tetrahydroisoquinoline hydrochloride monohydrate diastereoisomer B Prepared as Ex. No. 45, from 4.4 g (15.04 mmoles) of 1-(pyrrolidin-1-yl)methyl-4-phenyl-1,2,3,4-tetrahydroisoquinoline (2:1 mixture of diastereoisomeric diamines), 1.5 g (15.04 mmoles) of anhydrous potassium carbonate and 4.01 g (17.94 mmoles) of 3,4-dichlorophenylacetyl chloride in 100 ml of dry chloroform.

The work up of the reaction was carried out in the same manner described in Ex. No. 45 and the chromatographic column was eluted with a mixture of Et2O-

/MeOH/32% NH$_4$OH solution 20:1:0.1, to afford 4.8 g of the diastereoisomeric amides mixture, which was dissolved in 50 ml of acetone and the solution brought to acidic pH with HCl/diethyl ether. The precipitate was filtered and dissolved in the minimum amount of acetone containing 3% of EtOH. The salt precipitated after few days was filtered, washed and dried, to yield 180 mg of the title compound (the most polar product).

$C_{28}H_{28}Cl_2N_2O \cdot HCl \cdot H_2O$

M.P.=207° C.
M.W.=533.915

Elemental analysis: Calcd. C, 62.98; H, 5.85; N, 5.24; Found C, 63.02; H, 5.75; N, 5.10.

I.R. (KBr) : 1640 (s), 1440,1415 (m) cm$^{-1}$

EXAMPLE 51

1-(pyrrolidin-1-yl)methyl-2-(3,4-dichlorophenyl)acetyl-4-phenyl-1,2,3,4-tetrahydroisoquinoline hydrochloride acetone diastereoisomer A The mother liquors of the crystallization of the Example No. 50 were concentrated in vacuo to dryness and the residue dissolved in acetone. The least polar product was crystallized on standing, to yield 570 mg of the title compound. C . HCl . C$_3$H$_6$0

M.P.=166° C.
M.W.=573.977

Elemental analysis: Calcd. C, 64.86; H, 6.15; N, 4.88; Found C, 64.67; H, 6.02; N, 4.97.

I.R. (KBr) : 1715 (m), 1645 (s), 1445 (m) cm$^{-1}$

N.M.R. (CDCl$_3$) , δ11.70 (s broad, 1H); 6.70–7.45 (m, 12H) 6.10 (dd, 1H); 2.80–4.30 (m, 7H); 1.88–2.75 (m, 8H).

EXAMPLE 52

1-(pyrrolidin-1-yl)methyl-2-(3,4-dichlorophenyl)acetyl-5-acetoxy-1,2,3,4-tetrahydroisoquinoline hydrochloride 600 mg (1.32 mmoles) of the compound of the Ex. No. 5 (as hydrochloride) were heated one hour at 40° C. with 3 ml of acetic anhydride and 2 ml of CF$_3$COOH.

The reaction mixture was concentrated in vacuo to dryness. The residue was dissolved in ethyl acetate and the solution washed twice with a s.s. of NaHCO$_3$.

The solvent was evaporated in vacuo to dryness and the residual oil was chromatographed on silica gel, eluting with CH$_2$Cl$_2$, to afford 580 mg of the free base, which was dissolved in 20 ml of acetone and the solution brought to acidic pH with HCl/diethyl ether.

The precipitate was filtered, washed and dried, to yield 420 mg of the title compound.

$C_{24}H_{26}Cl_2N_2O_3 \cdot HCl$

M.P.=231°–233° C.
M.W.=497.843

Elemental analysis: Calcd. C,57.90; H,5.47; N,5.63; Cl,21.37 Found C, 57.81; H,5.55; N,5.57; Cl,21.19.

I.R. (KBr) : 1770 (s), 1638 (s), 1195 (s) cm$^{-1}$

EXAMPLE 53

(+)-1-(pyrrolidin-1-yl)methyl-2-(3,4-dichlorophenyl)acetyl-5-hydroxy-1,2,3,4-tetrahydroisoquinoline hydrochloride 0.85 g (2.15 mmoles) of crude (+)-1-(pyrrolidin-1-yl)methyl5-hydroxy-1,2,3,4-tetrahydroisoquinoline dihydrobromide were dissolved in 50 ml of chloroform, containing 1 ml of water and 2.5 g (18.12 mmoles) of potassium carbonate.

1.48 g (6.62 mmoles) of 3,4-dichlorophenyl acetyl chloride, dissolved in 10 ml of chloroform, were added dropwise at room temperature.

After three hours 10 ml of water were added and the organic layer was separated and concentrated in vacuo to dryness. The residue was dissolved in 35 ml of 5% HCl solution, containing 40% of ethanol and left overnight.

The solvent was evaporated in vacuo to dryness and the residue was treated with 32% NH$_4$OH solution, extracted with methylene chloride and chromatographed on silica gel, eluting with CH$_2$Cl$_2$ containing increasing amounts of MeOH (0.1 2.5%) , to afford 0.724 g of the free base, which gave an $[\alpha]_D^{20}=+24.79$ (C=1, MeOH)

This compound was dissolved in 20 ml of acetone and the solution brought to acidic pH with HCl/diethyl ether.

The precipitate was filtered, washed and dried, to yield 0.718 g of the title compound.

$C_{22}H_{24}Cl_2N_2O_2 \cdot HCl$

M.P.=248° C.
M.W.=455.807
$[\alpha]_D^{20}=+13.4$ (C=1, MeOH).

EXAMPLE 54

(−)-1-(pyrrolidin-1-yl)methyl-2-(3,4-dichlorophenyl)acetyl-5-hydroxy-1,2,3,4-tetrahydroisoquinoline hydrochloride Prepared as Ex. No. 53, from 0.75 g (1.91 mmoles) of crude (−)-1-(pyrrolidin-1-yl)methyl-5-hydroxy-1,2,3,4-tetrahydroisoquinoline dihydrobromide.

The work up of the reaction mixture and the silica gel chromatographic column were carried out as described in Ex. No. 53, to afford 0.621 g of the free base, which gave an $[\alpha]_D^{20}=-23.99$ (C=1, MeOH)

This compound was dissolved in 20 ml of acetone and the solution brought to acidic pH with HCl/diethyl ether. The precipitate was filtered, washed and dried, to yield 0.593 g of the title compound.

$C_{22}H_{24}Cl_2N_2O_2 \cdot HCl$

M.P.=247° C.
M.W.=455.807
$[\alpha]_D^{20}=-13.4$ (C=1, MeOH).

EXAMPLE 55

1-(pyrrolidin-1-yl)methyl-2-(3,4-dichlorobenzoyl)-5-hydroxy-1,2,3,4-tetrahydroisoquinoline Prepared as Ex. N. 33, from 1.1 g (4.73 mmoles) of 1-(pyrrolidin-1-yl)methyl-5-hydroxy-1,2,3,4-tetrahydroisoquinoline and 1.5 g (7.15 mmoles) of 3,4-dichlorobenzoyl chloride in 80 ml of dry chloroform, at −10° C.

The reaction mixture was allowed to reach room temperature and left overnight.

The solvent was evaporated in vacuo, the residue taken up with diluite HCl and extracted with diethyl ether.

The acqueous layer was treated with NH$_4$OH and extracted with methylene chloride.

The organic solution was dried over Na$_2$SO$_4$ and concentrated in vacuo to dryness.

Crystallization from acetone gave 1.53 g of the title compound.

$C_{21}H_{22}Cl$

M.P.=161°–163° C.
M.W.=405.316

Elemental analysis: Calcd. C,62.22; H,5.47; N,6,91; Cl,17.49; Found C,62.27; H,5.52; N,6,80; Cl,17.46.

I.R. (KBr) : 1630 (s) cm$^{-1}$

EXAMPLE 56

1-(pyrrolidin-1-yl) methyl-2-(2-thiophencarbonyl)-5-hydroxy-1,2,3,4-tetrahydroisoquinoline Prepared as Ex. N° 55, from 0.88 g (3.78 mmoles) of 1-(pyrrolidin-1-yl) methyl-5-hydroxy-1,2,3,4-tetrahydroisoquinoline and 0.83 g (5.66 mmoles) of 2-thiophene carbonyl chloride in 60 ml of dry chloroform, at −10° C.

The work up of the reaction mixture was carried out in the same manner of the example 55. Crystallization from acetone gave 1.1 g of the title compound.

$C_{19}H_{22}N_2O_2S$

M.P. = 185°–186° C.
M.W. = 342.448
I.R. (KBr) : 1635 (s) cm$^{-1}$

The structures, molecular formulae and melting points of Examples 1 to 56 are summarised in Table I.

(In Examples 1 to 31, $R_{6a}$ in formula (I) is hydrogen, so is omitted from the table).

TABLE I

| EXAMPLE No. | R | R1 | R2 | R3 | R4 | R5 | R6 | MOLECULAR FORMULA | MELTING POINT (°C.) |
|---|---|---|---|---|---|---|---|---|---|
| 1 CIS |  | ⌒ |  | H | CH$_3$ | H | H | C$_{23}$H$_{26}$Cl$_2$N$_2$O.HCl.½H$_2$O | 185–187 |
| 2 TRANS | " | " |  | " | " | " | " | C$_{23}$H$_{26}$Cl$_2$N$_2$O.HCl.½H$_2$O.CH$_3$COCH$_3$ | 115–118 |
| 3 TRANS | " | " |  | " | " | " | " | C$_{23}$H$_{26}$Cl$_2$N$_2$O.HCl | 214–217 |
| 4 CIS | " | " |  | " | H | CH$_3$ | " | C$_{23}$H$_{26}$Cl$_2$N$_2$O.HCl | 220–222 |
| 5 | " | " |  | " | " | H | 5-OH | C$_{22}$H$_{24}$Cl$_2$N$_2$O$_2$ | 165–167 |
| 6 | " | " |  | " | " | " | 5-OCH$_3$ | C$_{23}$H$_{26}$Cl$_2$N$_2$O$_2$ | 127–129 |
| 7 | " | " |  | " | " | " | 5-Cl | C$_{22}$H$_{23}$Cl$_3$N$_2$O.HCl | 226–228 |
| 8 | " | " |  | " | " | " | 5-F | C$_{22}$H$_{23}$Cl$_2$FN$_2$O.HCl | 235–237 |
| 9 | 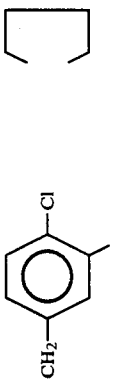 | ⌒ |  | H | H | H | 5-CH$_3$ | C$_{23}$H$_{26}$Cl$_2$N$_2$O.HCl | 220–222 |
| 10 | " | " |  | " | " | " | 5-OH | C$_{20}$H$_{22}$Cl$_2$N$_2$O$_2$ | 163–164 |
| 11 | " | " |  | " | " | " | 5-OCH$_3$ | C$_{21}$H$_{24}$Cl$_2$N$_2$O$_2$ | 109–111 |
| 12 | " | " |  | " | " | " | 5-Cl | C$_{20}$H$_{21}$Cl$_3$N$_2$O.HCl | 241–244 |
| 13 | " | " |  | " | " | " | 6-OH | C$_{20}$H$_{22}$Cl$_2$N$_2$O$_2$ | 199–200 |
| 14 | " | " |  | " | " | " | 6-OCH$_3$ | C$_{21}$H$_{24}$Cl$_2$N$_2$O$_2$ | 239–240 |
| 15 | " | " |  | " | " | " | 6-Cl | C$_{20}$H$_{21}$Cl$_3$N$_2$O.HCl | 241–242 |
| 16 | " | ⌒ |  | " | " | " | 6-OH | C$_{22}$H$_{24}$Cl$_2$N$_2$O$_2$ | 207–208 |
| 17 | " | " |  | " | " | " | 6OCH$_3$ | C$_{23}$H$_{26}$Cl$_2$N$_2$O$_2$.HCl | 196–198 |
| 18 | " | " |  | " | H | H | 6-Cl | C$_{22}$H$_{23}$Cl$_3$N$_2$O.HCl | 222–224 |
| 19 | " | " |  | " | " | " | 7-OH | C$_{22}$H$_{24}$Cl$_2$N$_2$O$_2$ | 147–149 |
| 20 | " | " |  | " | " | " | 7-OCH$_3$ | C$_{23}$H$_{26}$Cl$_2$N$_2$O$_2$.HCl.½H$_2$O | 110–111 |
| 21 | " | " |  | " | " | " | 7-Cl | C$_{22}$H$_{23}$Cl$_3$N$_2$O.HCl | 275–278 |
| 22 | " | CH$_3$ | CH$_3$ | " | " | " | 7-OH | C$_{20}$H$_{22}$Cl$_2$N$_2$O$_2$.¼EtOAc | 129–131 |

TABLE I-continued

| | R1 R2 | R3 | R4 | R5 | R6 | R6a | | MOLECULAR FORMULA | | |
|---|---|---|---|---|---|---|---|---|---|---|
| 23 | | | | | | | 7-OCH$_3$ | C$_{21}$H$_{24}$Cl$_2$N$_2$O$_2$.HCl | | 209-211 |
| 24 | " | | | | | | 7-Cl | C$_{20}$H$_{21}$Cl$_3$N$_2$O.HCl.½EtOH | | 258-260 |
| 25 | " | | | | | | 8-OH | C$_{22}$H$_{24}$Cl$_2$N$_2$O$_2$ | | 151-153 |
| 26 | (ring) | | | | | | 8-OCH$_3$ | C$_{23}$H$_{26}$Cl$_2$N$_2$O$_2$.HCl | | 248-250 |
| 27 | (ring) | | | H | | H | 8-Cl | C$_{22}$H$_{23}$Cl$_3$N$_2$O.HCl.¼H$_2$O | | 231-234 |
| 28 DIAST.A | " | CH$_3$ | CH$_3$ | | CH$_3$ | | H | C$_{23}$H$_{26}$Cl$_2$N$_2$O | | 148-150 |
| 29 DIAST.B | " | " | " | | " | | " | C$_{23}$H$_{26}$Cl$_2$N$_2$O | | 108-110 |
| 30 DIAST.A | " | CH$_3$ | CH$_3$ | | " | | " | C$_{21}$H$_{24}$Cl$_2$N$_2$O | | 143-144 |
| 31 DIAST.B | " | " | " | | " | | " | C$_{21}$H$_{24}$Cl$_2$N$_2$O | | 124-126 |

| Example N° | R | R1 R2 | R3 | R4 | R5 | R6 | R6a | MOLECULAR FORMULA | MELTING POINT (°C.) | ROTATORY POWER [α]$_D^{20}$ (C = 1, MeOH) | ROTATORY POWER OF THE CORRESPONDING FREE BASE [α]$_D^{20}$ (C = 1, CHCl$_3$) |
|---|---|---|---|---|---|---|---|---|---|---|---|
| 32 | 2,4-diCl-benzyl | (ring) | H | H | H | 5-SCH$_3$ | H | C$_{23}$H$_{26}$Cl$_2$N$_2$OS.HCl | 171 | — | — |
| 33 | 4-CF$_3$-benzyl | (ring) | H | H | H | 5-OCH$_3$ | H | C$_{24}$H$_{27}$F$_3$N$_2$O$_2$.HCl | 236-238 | — | — |
| 34 | 4-CF$_3$-benzyl | (ring) | H | H | H | 5-OH | H | C$_{23}$H$_{25}$F$_3$N$_2$O$_2$.HCl.¼H$_2$O | 164-166 | — | — |
| 35 | 4-CF$_3$-benzyl | (ring) | H | H | H | 5-OCH$_3$ | H | C$_{25}$H$_{29}$F$_3$N$_2$O$_2$.HCl | 231-233 | — | — |

TABLE I-continued

| No. | Ar | Ring | | | | | Formula | mp | | |
|---|---|---|---|---|---|---|---|---|---|---|
| 36 | —CH₂-(2,3-diCl-C₆H₃) | cyclohexyl | H | H | 5-OCH₃ | H | $C_{24}H_{28}Cl_2N_2O_2 \cdot HCl$ | 238–240 | — | — |
| 37 | —CH₂-(4-CF₃-C₆H₄) | cyclohexyl | H | H | 5-OH | H | $C_{24}H_{27}F_3N_2O_2 \cdot HCl$ | 168 | — | — |
| 38 | —CH₂-(2,3-diCl-C₆H₃) | cyclohexyl | H | H | 5-OH | H | $C_{23}H_{26}Cl_2N_2O_2 \cdot HCl$ | 170 | — | — |
| 39 | —CH₂-(2,3-diCl-C₆H₃) | cyclopentyl | H | H | 5-OCH₃ | 6-OCH₃ | $C_{24}H_{28}Cl_2N_2O_3 \cdot HCl$ | 232–235 | — | — |
| 40 | —CH₂-(2,3-diCl-C₆H₃) | cyclopentyl | H | H | 5-OH | 6-OH | $C_{22}H_{24}Cl_2N_2O_3 \cdot HCl$ | 241–243 | — | — |
| 41 | —CH₂-(2,3-diCl-C₆H₃) | cyclopentyl | H | CH₃ | H | H | $C_{23}H_{26}Cl_2N_2O \cdot L(+)C_4H_6O_6$ | 202 | +17.65 | +17.38 |
| 42 | —CH₂-(2,3-diCl-C₆H₃) | cyclopentyl | H | CH₃ | H | H | $C_{23}H_{26}Cl_2N_2O \cdot D(-)C_4H_6O_6$ | 201–202 | −17.81 | −17.70 |

TABLE I-continued

| | | | | | | | | |
|---|---|---|---|---|---|---|---|---|
| 43 | ![3,4-dichlorobenzyl] | H | H | CH₃ | H | C₂₃H₂₆Cl₂N₂O.L(+)C₄H₆O₆ | 185 | +23.28 | +25.00 |
| 44 | ![3,4-dichlorobenzyl] | H | H | CH₃ | H | C₂₃H₂₆Cl₂N₂O.D(−)C₄H₆O₆ | 185 | −23.76 | −25.48 |
| 45 DIAST.A | ![3,4-dichlorobenzyl] | H | CH₃ | CH₃ | H | C₂₄H₂₈Cl₂N₂O | 126–129 | — | — |
| 46 DIAST.B | ![3,4-dichlorobenzyl] | H | CH₃ | CH₃ | H | C₂₄H₂₈Cl₂N₂O | 117–119 | — | — |
| 47 DIAST.C | ![3,4-dichlorobenzyl] | H | CH₃ | CH₃ | H | C₂₄H₂₈Cl₂N₂O.HCl | 106 | — | — |
| 48 DIAST.A | ![3,4-dichlorobenzyl] | H | CH₃ | CH₃ | H | C₂₅H₃₀Cl₂N₂O | 130–132 | — | — |
| 49 DIAST.B | ![3,4-dichlorobenzyl] | H | CH₃ | CH₃ | H | C₂₅H₃₀Cl₂N₂O | 136–137 | — | — |

TABLE I-continued

| # | | | | | | | | |
|---|---|---|---|---|---|---|---|---|
| 50 DIAST.B | 2,3-Cl₂-C₆H₃-CH₂- | H | H | phenyl | H | H | C₂₈H₂₈Cl₂N₂O.HCl.H₂O | 207 | — | — |
| 51 DIAST.A | 2,3-Cl₂-C₆H₃-CH₂- | H | H | phenyl | H | H | C₂₈H₂₈Cl₂N₂O.HCl.CH₃COCH₃ | 166 | — | — |
| 52 | 2,3-Cl₂-C₆H₃-CH₂- | H | H | H | 5-OCOCH₃ | H | C₂₄H₂₆Cl₂N₂O₃.HCl | 231–233 | — | — |
| 53 | 2,3-Cl₂-C₆H₃-CH₂- | H | H | H | 5-OH | H | C₂₂H₂₄Cl₂N₂O₂.HCl | 248 | +13.40 | +24.79 |
| 54 | 2,3-Cl₂-C₆H₃-CH₂- | H | H | H | 5-OH | H | C₂₂H₂₄Cl₂N₂O₂.HCl | 247 | −13.40 | −23.99 |
| 55 | 2,3-Cl₂-C₆H₃- | H | H | H | 5-OH | H | C₂₁H₂₂Cl₂N₂O₂ | 161–163 | — | — |
| 56 | thien-2-yl | H | H | H | 5-OH | H | C₁₉H₂₂N₂O₂S | 185–186 | — | — |

The pharmacological activity of the compounds of this invention is illustrated by various in vitro and in vivo models, using the following test procedures, in which the mousetail flick test demonstrates analgesic activity. The results are summarised in Table 2.

PHARMACOLOGICAL TESTS (A) P-phenylquinone-induced abdominal writhing test in mice The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25–36g body weight, were used. Animals were allowed food and water ad libitum and were randomized into groups of 10 prior to experimentation. Test compounds were dissolved in either distilled water or distilled water plus 0.1 M AMS, and administered by the subcutaneous route in a final volume of 10 ml/Kg. Control animals received 10 ml/Kg of the appropriate vehicle alone. Following a pretreatment period of 20 min., mice were injected intraperitoneally with p-phenylquinone, 2 mg/Kg at 37° C. in a final volume of 10 mg/Kg. Next, the mice were placed, in groups of 3, in a compartmented perspex box maintained at room temperature and were observed for a period of 8 min. During this period the number of abdominal writhing responses per animal were recorded where writhing consists of an intermittent contraction of the abdomen associated with hind leg extension.

The degree of antinociceptive protection afforded by the test compound was determined as the mean number of writhing responses observed in the treated group (T) expressed as a percentage of the mean number of writhing responses in the control group (C) according to the following formula:

$[1-(T/C] \times 100\% = \%$ graded protection (B) Tail-flick test in mice

The methodology employed is based on that described by D'Amour and Smith, J. Pharmacol. Exp. Ther. 72, 74/1941.

Male Charles River mice (Swiss Strain), 22–34g body weight were used. Animals were allowed food and water ad libitum and were randomized into groups of 10 prior to experimentation. Before administration of the test compound, the reaction time of each animal was determined by focusing a beam of light onto the tail, eliciting a reflex withdrawal after a certain latency; only mice exhibiting a latency between 3–8 sec. were used subsequently in the evaluation of drug effects.

Test compounds were dissolved in either distilled water or distilled water plus 0.1 M AMS and administered by the subcutaneous route in a final volume of 10 ml/Kg. Control animals received 10 ml/kg of the appropriate vehicle alone. Following a pretreatment period of 30 min., the mice were again placed under the heat source and the reaction tine re-determined.

Percentage quantal protection was determined as the number of mice in which the reaction time was doubled compared to pretreatment values, expressed as a percentage of the total number of mice in the group.

RECEPTOR AFFINITY STUDY

Tissue preparation

Radio receptor binding to $\mu$ and K sites is performed on fresh guinea pig brain homogenate prepared according to Kosterlitz. (1981).

Whole brain without cerebellum is homogenized in 50 mM, Tris-buffer (pH 7.4 at 0° C.) and centrifuged at $49,000 \times g \times 10$ min.

The pellet is then resuspended in the same buffer, incubated at 37° C. for 45 min. and centrifuged again. 1.9ml of the final homogenate (1:100 in Tris-pH 7.4, 0° C.) is used for the binding assay. Binding to $\delta$ sites (Magnan J., 1982) 1 3H [D-Ala2, MePhe4, Gly-o15]Enkephalin (3H-DAGO), an enkephalin analogue that binds selectively to receptor, is added to the biological substrate and incubated at 25° C. for 40 min., filtered through Whatman GF-C and washed with ice-cold Tris-buffer. The filters are then dryed, solubilized in Filtercount and the radioactivity monitored. Non specific binding is determined in the presence of 10–6M Naloxone. 1 Binding to K sites (Magnan J., 1982)

The binding to the K-sites is performed using 3H-Ethyl Ketocyclazocine, a non-selective benzomorphan compound which binds to $\mu$, $\delta$ and K-sites, in the presence of 100nM of unlabelled DAGO and 100nM of the enkephalin analogue [DAla$^2$-DLeu$^5$]Enkephalin (DADLE), to prevent $\mu$ and $\delta$ binding respectively.

Final homogenate with solutions of the cold ligand and of the labelled ligand is incubated for 40 min. at 25° C., filtered through Whatman GF/C glass filter discs and washed.

The radioactivity bound to the filters is counted by liquid scintillation spectrophotometry.

The non-specific binding is determined in the presence of 500nM of the benzomorphan non-selective compound Mr 2266.

Binding to $\delta$ sites (Magnan J., 1982)

For binding experiments, 3H-DADLE, which binds to $\mu$ and $\delta$ sites, is used in the presence of 30nm of unlabelled DAGO to prevent $\mu$ binding. A concentration of radioligand near KD is used in the binding assays evaluating compounds of the invention. Non-specific binding is determined by addition of Mr 2266 2.5$\mu$M.

The tubes are incubated for 40 min at 25° C. and bound ligand is separated from free by filtration through Whatman GF/G filters. The level of bound radioactivity on the filters is measured by liquid scintillation after solubilization in Filtercount.

The equilibrium dissociation constant (KD) and the maximum binding capacity (Bmax) are determined from the analysis of saturation curves, while the inhibition constant (Ki) is determined from the analysis of competition experiments (Hill 1910; Scatchard 1949; Cheng and Prusoff 1973; Gillan et al. 1980).

Published references are summarised as follows:

Hill, A. V. (1910) : J. Physiol.40, IV–VIII (1910)

Scatchard G. (1949): Ann. N.Y. Acad.Sci., 51, 660–674

Cheng and Prusoff W. H.(1973) : Biochem. Pharmac.22, 3099–3102

Gillan M. G. C., Kosterlitz H. W.:Br.J. pharmac. 70, and Paterson S. Y. (1980) 481–490

Kotsterliz H. W., Paterson S. Y. :Br.J. Pharmac. 73, and Robson L. E. (1981) 939–949

Magnan J., Paterson S. Y., :Arch. Pharmacol. 319, Tavani A., and Kosterlits 197-205 H. W. (1982)

TABLE 2

| Example No. | MOUSE WRITHING ED50 mg/kg SUBCUTANEOUS* | MOUSE TAIL-FLICK ED50 mg/kg | OPIATE RECEPTORS BINDING Ki = nM KAPPA | MU |
|---|---|---|---|---|
| 1 | 0.021 | 0.033 | 2.65 | 14.9 |
| 2 | — | >1 | 1-50 | — |
| 3 | 0.036 | 0.046 | 4.79 | 122 |
| 4 | 0.282 | 0.459 | 14 | 1146 |
| 5 | 0.005 | 0.009 | 0.423 | 0.69 |
| 6 | 0.047 | 0.054 | 4.01 | 277 |
| 7 | — | 0.836 | 43.6 | 1580 |
| 10 | — | 0.088 | 0.42 | 3.67 |
| 16 | — | 0.240 | 1.54 | 102 |
| 27 | — | 0.092 | 5.46 | 369 |
| 32 | 0.202 | 0.365 | | 442 |
| 33 | 0.060 | 0.306 | | 142 |
| 34 | 0.0023 | 0.011 | | 0.59 |
| 35 | 0.204 | 0.689 | | ca 1000 |
| 36 | 0.163 | 0.924 | | ca 1000 |
| 37 | 0.0013 | 0.007 | | 5.38 |
| 38 | 0.004 | 0.010 | | 11.4 |
| 39 | — | >1 | | — |
| 40 | 0.429 | 0.461 | | 49.2 |
| 42 | 0.010 | 0.021 | 2.23 | 11.1 |
| 44 | 0.013 | 0.025 | | 56.5 |
| 46 | 0.011 | 0.048 | | |
| 47 | — | 8.9 | | |
| 49 | 0.038 | 0.077 | | |
| 50 | — | 20 | | |
| 52 | 0.005 | 0.024 | | |
| 54 | 0.0022 | 0.006 | | |

*Calculated as the free base

We claim:

1. A compound, or a solvate or salt thereof, of formula (I):

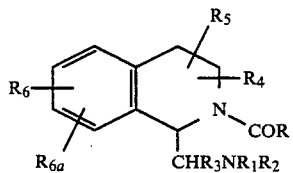

in which:
RCO is an acyl group in which the group R has the formula (II):

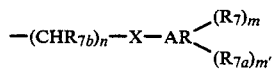

in which
n is 0, 1 or 2;
m is 0, 1 or 2;
m' is 0, 1 or 2, provided m+m'≦2
X is a direct bond, or O S or NR$_8$ in which R$_8$ is hydrogen or C$_{1-6}$ alkyl;
Ar is either a single or fused ring carbocyclic aromatic group having 6 to 12 ring atoms or a single or fused ring heterocyclic aromatic group have 5 to 12 ring atoms, comprising up to four hetero atoms in each ring selected from oxygen, nitrogen and sulphur;
each of R$_7$ and R$_{7a}$ is C$_{1-6}$ alkyl, C$_{2-6}$ alkenyl, C$_{2-6}$ alkynyl, C$_{1-6}$ haloalkyl, C$_{2-6}$ haloalkenyl, C$_{2-6}$ haloalkynyl, phenyl, phenylalkyl, hydroxy, C$_{1-6}$ alkoxy, thiol, C$_{1-6}$ alkylthio, C$_{1-6}$ haloalkoxy, C$_{1-6}$ haloalkylthio, halogen, NO$_2$, CN, CF$_3$, —OCF$_3$, —OCHF$_2$, —OCF$_2$CF$_2$H, —OCCl$_2$CF$_3$, —COOR$_9$, —CONR$_{10}$R$_{11}$, —SO$_3$R$_{12}$, —SO$_2$NR$_{13}$R$_{14}$ or —COR$_{15}$ in which each of R$_9$ to R$_{15}$ is independently hydrogen, C$_{1-6}$ alkyl, phenyl or phenylalkyl;
or, when m is 2 and m' is 0, two R$_7$'s form a C$_{2-6}$ polymethylene group;
and R$_{7b}$ is hydrogen or C$_{1-6}$ alkyl;
R$_1$ and R$_2$ are independently hydrogen, C$_{1-6}$alkyl, C$_{2-6}$ alkenyl, C$_{3-6}$ cycloalkyl or C$_{4-12}$ cycloalkylalkyl groups or together form a C$_{2-8}$ branched or linear polymethylene or C$_{2-6}$ alkenylene group optionally interrupted with an oxygen or sulphur atom to form an ether or thioether, respectively;
R$_3$ is hydrogen, C$_{1-6}$ alkyl, or phenyl, or R$_3$ together with R$_1$ forms a —(CH$_2$)$_3$— or —(CH$_2$)$_4$—, group;
R$_4$ and R$_5$, which may be the same or different and may be attached to the same or different carbon atoms of the isoquinoline nucleus, are each hydrogen, halogen, hydroxy, C$_{1-6}$ alkyl, phenyl, or R$_4$ together with R$_5$ form a —(CH$_2$)$_p$— group, where p is an integer from 1 to 5 and one or more of the —(CH$_2$)— moieties is optionally substituted by a C$_{1-6}$ alkyl group; and
R$_6$ and R$_{6a}$, which may be the same or different, are each hydrogen, C$_{1-6}$ alkyl, —CH$_2$OR$_{6b}$, halogen, hydroxy, C$_{1-6}$ alkoxy, C$_{1-6}$ alkoxycarbonyl, thiol, C$_{1-6}$ alkylthio,

—NHCOR$_{6d}$, —NHSO$_2$R$_{6e}$, —CH$_2$SO$_2$NR$_{6f}$R$_{6g}$, in which each of R$_{6b}$ to R$_{6g}$ is independently hydrogen, C$_{1-6}$ alkyl, phenyl or phenylalkyl with the proviso that R$_4$, R$_5$, R$_6$ and R$_{6a}$ are not simultaneously hydrogen.

2. A compound according to claim 1, in which each of R$_1$ and R$_2$ is methyl, ethyl, propyl, butyl pentyl or hexyl.

3. A compound according to claim 1, in which R$_1$ and R$_2$ together form a propylene, butylene, pentylene or hexylene group, or a —CH$_2$—CH=CH—CH$_2$— group.

4. A compound according to claim 1 in which Ar is phenyl.

5. A compound according to claim 1 in which R$_7$ or R$_{7a}$ is chlorine, bromine, NO$_2$ or CF$_3$ in the meta- or paraposition.

6. A compound according to claim 1 in which R$_6$ or R$_{6a}$ is hydroxy, methyl, methoxy, chloro, fluoro, methylthio or methoxy carbonyl.

7. A compound selected from the group consisting of:
1-(pyrrolidin-1-yl)methyl-2-(3,4-dichlorophenyl)acetyl-3-methyl-1,2,3,4-tetrahydroisoquinoline;
1-(pyrrolidin-1-yl)methyl-2-(3,4-dichlorophenyl)acetyl-4-methyl-1,2,3,4-tetrahydroisoquinoline;
1-(pyrrolidin-1-yl)methyl-2-(3,4-dichlorophenyl)acetyl-5-hydroxy-1,2,3,4-tetrahydroisoquinoline;
1-(pyrrolidin-1-yl)methyl-2-(3,4-dichlorophenyl)acetyl-5-methoxy-1,2,3,4-tetrahydroisoquinoline;
1-(pyrrolidin-1-yl)methyl-2-(3,4-dichlorophenyl)acetyl-5-chloro-1,2,3,4-tetrahydroisoquinoline;
1-(pyrrolidin-1-yl)methyl-2-(3,4-dichlorophenyl)acetyl-5-fluoro-1,2,3,4-tetrahydroisoquinoline;

1-(pyrrolidin-1-yl)methyl-2-(3,4-dichlorophenyl)acetyl-5-methyl-1,2,3,4-tetrahydroisoquinoline;
1-dimethylaminomethyl-2-(3,4-dichlorophenyl)acetyl-5-hydroxy-1,2,3,4-tetrahydroisoquinoline;
1-dimethylaminomethyl-2-(3,4-dichlorophenyl)acetyl-5-methoxy-1,2,3,4-tetrahydroisoquinoline;
1-dimethylaminomethyl-2-(3,4-dichlorophenyl)acetyl-5-chloro-1,2,3,4-tetrahydroisoquinoline;
1-dimethylaminomethyl-2-(3,4-dichlorophenyl)acetyl-6-hydroxy-1,2,3,4-tetrahydroisoquinoline;
1-dimethylaminomethyl-2-(3,4-dichlorophenyl)acetyl-6-methoxy-1,2,3,4-tetrahydroisoquinoline;
1-dimethylaminomethyl-2-(3,4-dichlorophenyl)acetyl-6-chloro-1,2,3,4-tetrahydroisoquinoline;
1-(pyrrolidin-1-yl)methyl-2-(3,4-dichlorophenyl)acetyl-6-hydroxy-1,2,3,4-tetrahydroisoquinoline;
1-(pyrrolidin-1-yl)methyl-2-(3,4-dichlorophenyl)acetyl-6-methoxy-1,2,3,4-tetrahydroisoquinoline;
1-(pyrrolidin-1-yl)methyl-2-(3,4-dichlorophenyl)acetyl-6-chloro-1,2,3,4-tetrahydroisoquinoline;
1-(pyrrolidin-1-yl)methyl-2-(3,4-dichlorophenyl)acetyl-7-hydroxy-1,2,3,4-tetrahydroisoquinoline;
1-(pyrrolidin-1-yl)methyl-2-(3,4-dichlorophenyl)acetyl-7-methoxy-1,2,3,4-tetrahydroisoquinoline;
1-(pyrrolidin-1-yl)methyl-2-(3,4-dichlorophenyl)acetyl-7-chloro-1,2,3,4-tetrahydroisoquinoline;
1-dimethylaminomethyl-2-(3,4-dichlorophenyl)acetyl-7-methoxy-1,2,3,4-tetrahydroisoquinoline;
1-dimethylaminomethyl-2-(3,4-dichlorophenyl)acetyl-7-hydroxy-1,2,3,4-tetrahydroisoquinoline;
1-dimethylaminomethyl-2-(3,4-dichlorophenyl)acetyl-7-chloro-1,2,3,4-tetrahydroisoquinoline;
1-(pyrrolidin-1-yl)methyl-2-(3,4-dichlorophenyl)acetyl-8-hydroxy-1,2,3,4-tetrahydroisoquinoline;
1-(pyrrolidin-1-yl)methyl-2-(3,4,-dichlorophenyl)acetyl-8-methoxy-1,2,3,4-tetrahydroisoquinoline;
1-(pyrrolidin-1-yl)methyl-2-(3,4-dichlorophenyl)acetyl-8-chloro-1,2,3,4-tetrahydroisoquinoline;
1-(pyrrolidin-1-yl)eth-1-yl-2-(3,4-dichlorophenyl)-acetyl-1,2,3,4-tetrahydroisoquinoline;
1-dimethylamino-eth-1-yl-2-(3,4-dichlorophenyl)-acetyl-1,2,3,4-tetrahydroisoquinoline;
1-(pyrrolidin-1-yl)methyl-2-(3,4-dichlorophenyl)acetyl-5-methylthio-1,2,3,4-tetrahydroisoquinoline;
1-(pyrrolidin-1-yl)methyl-2-(4-trifluoromethylphenyl)-acetyl-5-methoxy-1,2,3,4-tetrahydroisoquinoline;
1-(pyrrolidin-1-yl)methyl-2-(4-trifluoromethylphenyl)-acetyl-5-hydroxy-1,2,3,4-tetrahydroisoquinoline;
1-(piperidin-1-yl)methyl-2-(4-trifluoromethylphenyl)-acetyl-5-methoxy-1,2,3,4-tetrahydroisoquinoline;
1-(piperidin-1-yl)methyl-2-(3,4-dichlorophenyl)-acetyl-5-methoxy-1,2,3,4-tetrahydroisoquinoline;
1-(piperidin-1-yl)methyl-2-(4-trifluoromethylphenyl)-acetyl-5-hydroxy-1,2,3,4-tetrahydroisoquinoline;
1-(piperidin-1-yl)methyl-2-(3,4-dichlorophenyl)-acetyl-5-hydroxy-1,2,3,4-tetrahydroisoquinoline;
1-(pyrrolidin-1-yl)methyl-2-(3,4-dichlorophenyl)-acetyl-5,6-dimethoxy-1,2,3,4-tetrahydroisoquinoline;
1-(pyrrolidin-1-yl)methyl-2-(3,4-dichlorophenyl)-acetyl-5,6-dihydroxy-1,2,3,4-tetrahydroisoquinoline;
(+)-1-(pyrrolidin-1-yl)methyl-2-(3,4-dichlorophenyl)-acetyl-3-methyl-1,2,3,4-tetrahydroisoquinoline;
(−)-1-(pyrrolidin-1-yl)methyl-2-(3,4-dichlorophenyl)-acetyl-3-methyl-1,2,3,4-tetrahydroisoquinoline;
(+)-1-(pyrrolidin-1-yl)methyl-2-(3,4-dichlorophenyl)-acetyl-4-methyl-1,2,3,4-tetrahydroisoquinoline;
(−)-1-(pyrrolidin-1-yl)methyl-2-(3,4-dichlorophenyl)-acetyl-4-methyl-1,2,3,4-tetrahydroisoquinoline;
1-(pyrrolidin-1-yl)methyl-2-(3,4-dichlorophenyl)-acetyl-3,4-dimethyl-1,2,3,4-tetrahydroisoquinoline;
1-(piperidin-1-yl)methyl-2-(3,4-dichlorophenyl)-acetyl-3,4-dimethyl-1,2,3,4-tetrahydroisoquinoline;
1-(pyrrolidin-1-yl)methyl-2-(3,4-dichlorophenyl)-acetyl-4-phenyl-1,2,3,4-tetrahydroisoquinoline;
1-(pyrrolidin-1-yl)methyl-2-(3,4-dichlorophenyl)-acetyl-5-acetoxy-1,2,3,4-tetrahydroisoquinoline;
(+)-1-(pyrrolidin-1-yl)methyl-2-(3,4-dichlorophenyl)-acetyl-5-hydroxy-1,2,3,4-tetrahydroisoquinoline;
(−)-1-(pyrrolidin-1-yl)methyl-2-(3,4-dichlorophenyl)-acetyl-5-hydroxy-1,2,3,4-tetrahydroisoquinoline;
1-(pyrrolidin-1-yl)methyl-2-(3,4-dichlorobenzoyl)-5-hydroxy-1,2,3,4-tetrahydroisoquinoline;
1-(pyrrolidin-1-yl)methyl-2-(2-thiophencarbonyl)-5-hydroxy-1,2,3,4-tetrahydroisoquinoline.

8. A pharmaceutical composition comprising a compound according to claim 1, and a pharmaceutically acceptable carrier.

9. A composition according to claim 8 in unit dosage form.

10. A method of treating pain in mammals which comprises administering an effective, non toxic amount of a compound according to claim 1 to a sufferer.

* * * * *